(12) United States Patent
Matray et al.

(10) Patent No.: US 11,377,563 B2
(45) Date of Patent: Jul. 5, 2022

(54) IONIC POLYMERS COMPRISING FLUORESCENT OR COLORED REPORTER GROUPS

(71) Applicant: SONY CORPORATION, Tokyo (JP)

(72) Inventors: Tracy Matray, Snohomish, WA (US); Sharat Singh, Rancho Santa Fe, CA (US); Michael VanBrunt, Covington, WA (US)

(73) Assignee: Sony Corporation, Tokyo (JP)

( * ) Notice: Subject to any disclaimer, the term of this patent is extended or adjusted under 35 U.S.C. 154(b) by 608 days.

(21) Appl. No.: 16/307,876

(22) PCT Filed: Jun. 6, 2017

(86) PCT No.: PCT/US2017/036175
§ 371 (c)(1),
(2) Date: Dec. 6, 2018

(87) PCT Pub. No.: WO2017/214165
PCT Pub. Date: Dec. 14, 2017

(65) Prior Publication Data
US 2019/0300716 A1   Oct. 3, 2019

Related U.S. Application Data

(60) Provisional application No. 62/346,152, filed on Jun. 6, 2016.

(51) Int. Cl.
| | | |
|---|---|---|
| *C07F 9/09* | (2006.01) | |
| *C08K 5/00* | (2006.01) | |
| *C08K 5/3472* | (2006.01) | |
| *C08L 5/00* | (2006.01) | |
| *C08L 77/02* | (2006.01) | |
| *C09B 1/00* | (2006.01) | |
| *C09B 69/10* | (2006.01) | |
| *G01N 33/58* | (2006.01) | |

(52) U.S. Cl.
CPC .............. *C09B 69/109* (2013.01); *C07F 9/09* (2013.01); *C08K 5/0041* (2013.01); *C08K 5/3472* (2013.01); *C08L 5/00* (2013.01); *C08L 77/02* (2013.01); *C09B 1/002* (2013.01); *C09B 69/101* (2013.01); *C09B 69/102* (2013.01); *C09B 69/103* (2013.01); *G01N 33/582* (2013.01); *G01N 33/583* (2013.01); *G01N 33/585* (2013.01)

(58) Field of Classification Search
None
See application file for complete search history.

(56) References Cited

U.S. PATENT DOCUMENTS

| | | | |
|---|---|---|---|
| 4,450,305 A | 5/1984 | Kamhi | |
| 4,476,229 A | 10/1984 | Fino et al. | |
| 4,778,753 A | 10/1988 | Yamanishi et al. | |
| 5,053,054 A | 10/1991 | Kirchanski | |
| 5,268,486 A | 12/1993 | Waggoner et al. | |
| 5,318,894 A | 6/1994 | Pugia | |
| 5,582,977 A | 12/1996 | Yue et al. | |
| 5,994,143 A | 11/1999 | Bieniarz et al. | |
| 6,140,480 A | 10/2000 | Kool | |
| 6,171,859 B1 | 1/2001 | Herrnstadt et al. | |
| 6,218,108 B1 | 4/2001 | Kool | |
| 6,365,730 B1 | 4/2002 | Jennings et al. | |
| 6,380,431 B1 | 4/2002 | Whipple et al. | |
| 6,479,650 B1 | 11/2002 | Kool | |
| 6,514,700 B1 | 2/2003 | Singh | |
| 6,534,041 B1 | 3/2003 | Licha et al. | |
| 6,627,400 B1 | 9/2003 | Singh et al. | |
| 6,670,193 B2 | 12/2003 | Kool | |
| 6,716,452 B1 | 4/2004 | Piccariello et al. | |
| 6,852,709 B2 | 2/2005 | Leong et al. | |
| 7,038,063 B2 | 5/2006 | Lee et al. | |
| 7,060,708 B2 | 6/2006 | Piccariello et al. | |
| 7,172,907 B2 | 2/2007 | Chen et al. | |
| 7,423,133 B2 | 9/2008 | Kool et al. | |
| 7,667,024 B2 | 2/2010 | Mao et al. | |
| 7,897,684 B2 | 3/2011 | Bazan et al. | |
| 8,008,522 B2 | 8/2011 | Lukhtanov et al. | |
| 8,101,776 B2 | 1/2012 | Berens et al. | |
| 8,217,389 B2 | 7/2012 | Nakano et al. | |
| 8,349,308 B2 | 1/2013 | Yurkovetskiy et al. | |
| 8,354,515 B2 | 1/2013 | Ueno et al. | |

(Continued)

FOREIGN PATENT DOCUMENTS

| | | |
|---|---|---|
| CN | 103319378 A | 9/2013 |
| CN | 103319378 A | 9/2013 |

(Continued)

OTHER PUBLICATIONS

Sun et al. "High yield production of high molecular weight poly-(ethylene glycol)/α-cyclodextrin polyrotaxanes by aqueous one-pot approach" Polymer 2012, 53, 2884-2889. (Year: 2012).*

Teyssot et al. "Aromatic nitrogen donors for efficient copper(I)-NHC CuAAC under reductant-free conditions" Eur. J. Org. Chem. 2010, 18, 3507-3515. (Year: 2010).*

Drescher et al. "General synthesis and aggregation behavior of new single-chain bolaphospholipids: Variations in chain and headgroup structures" Chem. Eur. J. 2008, 14, 6796-6804. (Year: 2008).*

(Continued)

*Primary Examiner* — Amanda L. Aguirre

(74) *Attorney, Agent, or Firm* — Seed IP Law Group LLP

(57) ABSTRACT

Polymers comprising first and second fluorescent or colored moieties on the polymer backbone and two or more charged moieties on the polymer backbone between the first and second colored or fluorescent moieties are provided. The polymers are useful as fluorescent or colored dyes. Methods associated with preparation and use of such polymers are also provided.

14 Claims, No Drawings

(56) References Cited

U.S. PATENT DOCUMENTS

| | | |
|---|---|---|
| 8,431,545 B2 | 4/2013 | Kataoka et al. |
| 8,546,590 B2 | 10/2013 | Gall |
| 8,802,738 B2 | 8/2014 | Emrick |
| 8,895,023 B2 | 11/2014 | Rademacher et al. |
| 8,906,603 B2 | 12/2014 | Castro et al. |
| 9,085,799 B2 | 7/2015 | Bazan et al. |
| 9,150,782 B2 | 10/2015 | Lee et al. |
| 9,400,273 B1 | 7/2016 | Liu et al. |
| 9,545,447 B2 | 1/2017 | Wooley et al. |
| 9,649,389 B2 | 5/2017 | Groves et al. |
| 9,687,291 B2 | 6/2017 | Shimizu et al. |
| 9,689,877 B2 | 6/2017 | Matray et al. |
| 9,696,310 B2 | 7/2017 | Margulies et al. |
| 9,765,220 B2 | 9/2017 | Matray et al. |
| 9,822,134 B2 | 11/2017 | Segev |
| 9,851,359 B2 | 12/2017 | Matray et al. |
| 9,884,070 B2 | 2/2018 | Denardo et al. |
| 9,913,992 B2 | 3/2018 | Demarest et al. |
| 9,932,578 B2 | 4/2018 | Feinstein et al. |
| 9,939,454 B2 | 4/2018 | Dzubay et al. |
| 10,036,754 B2 | 7/2018 | Matray et al. |
| 10,191,060 B2 | 1/2019 | Chiu et al. |
| 10,435,563 B2 | 10/2019 | Matray et al. |
| 10,709,791 B2 | 7/2020 | Stayton et al. |
| 10,865,310 B2 | 12/2020 | Matray et al. |
| 10,866,244 B2 | 12/2020 | Matray et al. |
| 10,954,391 B2 | 3/2021 | Matray et al. |
| 10,989,715 B2 | 4/2021 | Matray et al. |
| 11,084,932 B2 | 8/2021 | Battrell et al. |
| 11,142,647 B2 | 10/2021 | Matray et al. |
| 2001/0018503 A1 | 8/2001 | Whipple et al. |
| 2002/0012947 A1 | 1/2002 | Bevers et al. |
| 2002/0099013 A1 | 7/2002 | Piccariello et al. |
| 2003/0054361 A1 | 3/2003 | Heller |
| 2003/0207208 A1 | 11/2003 | Uenishi |
| 2003/0207264 A1 | 11/2003 | Packard et al. |
| 2004/0014981 A1 | 1/2004 | Lugade et al. |
| 2004/0138467 A1 | 7/2004 | French et al. |
| 2004/0224372 A1 | 11/2004 | Li et al. |
| 2004/2417681 | 12/2004 | Whitten et al. |
| 2005/0054024 A1 | 3/2005 | Lawrence |
| 2005/0123935 A1 | 6/2005 | Haugland et al. |
| 2006/0008822 A1 | 1/2006 | Manoharan et al. |
| 2006/0035302 A1 | 2/2006 | Lee |
| 2006/0063186 A1 | 3/2006 | Benson et al. |
| 2007/0042398 A1 | 2/2007 | Peng et al. |
| 2007/0077549 A1 | 4/2007 | Buller et al. |
| 2007/0148094 A1 | 6/2007 | Uzgiris |
| 2007/0269902 A1 | 11/2007 | Beechem et al. |
| 2008/0227939 A1 | 9/2008 | Mizoshita et al. |
| 2009/0253792 A1 | 10/2009 | Mickle et al. |
| 2009/0299070 A1 | 12/2009 | Berens et al. |
| 2010/0039684 A1 | 2/2010 | Kolb et al. |
| 2010/0092386 A1 | 4/2010 | Segev |
| 2010/0129800 A1 | 5/2010 | Aymami Bofarull et al. |
| 2010/0192312 A1 | 8/2010 | Cremer et al. |
| 2011/0224516 A1 | 9/2011 | Romey et al. |
| 2012/0116079 A1 | 5/2012 | Lukhtanov et al. |
| 2013/0059343 A1 | 3/2013 | Cheung |
| 2013/0102021 A1 | 4/2013 | Beacham et al. |
| 2013/0119363 A1 | 5/2013 | Sasaki et al. |
| 2013/0137755 A1 | 5/2013 | Segev |
| 2013/0202536 A1 | 8/2013 | Mustaev et al. |
| 2013/0244891 A1 | 9/2013 | Waggoner et al. |
| 2015/0110715 A1 | 4/2015 | Eder et al. |
| 2015/0159198 A1 | 6/2015 | McGall et al. |
| 2015/0232615 A1 | 8/2015 | Kwiatkowski |
| 2015/0258217 A1 | 9/2015 | Caravan |
| 2016/0039850 A1 | 2/2016 | Segev |
| 2016/0176903 A1 | 6/2016 | Segev |
| 2016/0264737 A1 | 9/2016 | Bartholomew et al. |
| 2016/0327859 A1 | 11/2016 | Idei et al. |
| 2016/0347907 A1 | 12/2016 | Dose |
| 2017/0326233 A1 | 11/2017 | Demeule et al. |
| 2018/0065998 A1 | 3/2018 | Battrell et al. |
| 2018/0079909 A1 | 3/2018 | Matray et al. |
| 2018/0163052 A1 | 6/2018 | Matray et al. |
| 2018/0164322 A1 | 6/2018 | Matray et al. |
| 2018/0237641 A1 | 8/2018 | Battrell et al. |
| 2019/0016898 A1 | 1/2019 | Matray et al. |
| 2019/0136065 A1 | 5/2019 | Singh et al. |
| 2019/0144678 A1 | 5/2019 | Matray |
| 2019/0153232 A1 | 5/2019 | Matray et al. |
| 2019/0177549 A1 | 6/2019 | Matray et al. |
| 2020/0109287 A1 | 4/2020 | Matray et al. |
| 2020/0222554 A1 | 7/2020 | Matray et al. |
| 2020/0284798 A1 | 9/2020 | Matray et al. |
| 2020/0353089 A1 | 11/2020 | Matray |
| 2020/0353094 A1 | 11/2020 | Matray |
| 2020/0360526 A1 | 11/2020 | Matray |
| 2020/0392345 A1 | 12/2020 | Matray et al. |
| 2021/0032277 A1 | 2/2021 | Matray et al. |
| 2021/0032474 A1 | 2/2021 | Matray et al. |
| 2021/0095130 A1 | 4/2021 | Matray et al. |
| 2021/0096135 A1 | 4/2021 | Matray et al. |
| 2021/0109104 A1 | 4/2021 | Jackson et al. |
| 2021/0128591 A1 | 5/2021 | Matray |
| 2021/0128739 A1 | 5/2021 | Matray |
| 2021/0253864 A1 | 8/2021 | Matray et al. |
| 2021/0261782 A1 | 8/2021 | Matray et al. |
| 2021/0285953 A1 | 9/2021 | Matray et al. |
| 2021/0340380 A1 | 11/2021 | Matray et al. |
| 2021/0395530 A1 | 12/2021 | Matray et al. |

FOREIGN PATENT DOCUMENTS

| | | | |
|---|---|---|---|
| CN | 104072727 A | | 10/2014 |
| CN | 104072727 A | | 10/2014 |
| CN | 106589005 A | | 4/2017 |
| EP | 1 650 269 A2 | | 4/2006 |
| EP | 1 655 317 A1 | | 5/2006 |
| GB | 2 372 256 A | | 8/2002 |
| GB | 2 456 298 A | | 7/2009 |
| GB | 2 554 666 A | | 4/2018 |
| JP | 61207395 A | * | 9/1986 |
| JP | 4-282391 A | | 10/1992 |
| JP | H11505553 A | | 5/1999 |
| JP | 2000-17183 A | | 1/2000 |
| JP | 2004004048 A | | 1/2004 |
| JP | 2005503114 A | | 2/2005 |
| KR | 10-1041446 B1 | | 6/2011 |
| KR | 10-2015-0007795 A | | 1/2015 |
| SU | 1121931 A | | 4/1988 |
| WO | 95/02700 A1 | | 1/1995 |
| WO | 01/73123 A2 | | 10/2001 |
| WO | 02/22883 A1 | | 3/2002 |
| WO | 2009/015467 A1 | | 2/2009 |
| WO | 2010/026957 A1 | | 3/2010 |
| WO | 2013/012687 A2 | | 1/2013 |
| WO | 2014/147642 A1 | | 9/2014 |
| WO | 2014/159392 A1 | | 10/2014 |
| WO | 2015/027176 A1 | | 2/2015 |
| WO | 2015/109136 A2 | | 7/2015 |
| WO | 2017/173348 A1 | | 10/2017 |
| WO | 2017/177065 A2 | | 10/2017 |
| WO | 2018/060722 A1 | | 4/2018 |
| WO | 2019/071208 A1 | | 4/2019 |
| WO | 2021/062176 A2 | | 4/2021 |
| WO | 2021/067483 A1 | | 4/2021 |

OTHER PUBLICATIONS

Nakaya et al. "Diol with phospholipid-similar structure and its production method" JP 1986-207395 A. English machine translation [online][retrieved on Feb. 23, 2022]. Retrieved from <https://patentscope.wipo.int/search/en/detail.jsf?docId=JP263639642&_cid=P12-L04CIM-98617-1> (Year: 1985).*

U.S. Appl. No. 16/090,560, filed Oct. 1, 2018.

U.S. Appl. No. 16/440,677, filed Jun. 13, 2019.

"What is an Analyte?," Google Search, dated Mar. 22, 2018, retrieved from https://www.google.com/search?q-what+is+an+analyte&rlz-lClGCEB_enUS775US775&oq-what+is+an+analyte&aqs=chrome..69i57j0I5.32311j0j7&s . . . 2 pages.

(56) References Cited

OTHER PUBLICATIONS

Arian et al., "1,9-Dialkoxyanthracene as a $^1O_2$-Sensitive Linker," *J. Am. Chem. Soc.* 133:3972-3980, 2011.
Babitskaya et al., "Bromoacyl Analogues of Phosphatidylcholine with Intramolecular Fluorescence Quenching and Their Use as Substrates for Continuous Monitoring of Phospholipase $A_2$ Activity," *Applied Biochemistry and Microbiology* 40(4):351-356, 2004.
Becker et al., "New Thermotropic Dyes on Amino-Substituted Perylendicarboximides," *Chem. Eur. J.* 6(21):3984-3990, 2000.
Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016. (8 pages).
Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015, 1 page.
Bergstrom et al., "Potent Promise," *Innovations in Pharmaceutical Technology* 49:16-20, 2014.
Bergstrom et al., "XMT-1522 induces tumor regressions in preclinical models representing HER2-positive and HER2 low-expressing breast cancer," Mersana Therapeutics, Abstract P4-14-28, 2015, 1 page.
Braeckmans et al., "Three-dimensional fluorescence recovery after photobleaching with the confocal scanning laser microscope," *Biophysical Journal* 85:2240-2252, 2003.
Braga et al., "Intracellular macromolecular mobility measured by fluorescence recovery after photobleaching with confocal laser scanning microscopes," *Molecular Biology of the Cell* 15:4149-4760, 2004.
Brinkley, "A brief survey of methods for preparing protein conjugates with dyes, haptens and crosslinking reagents," *Bioconjugate Chem* 3:2-13, 1992.
CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975, (1 page).
Chong et al., "Oxygen Quenching of Pyrene-Lipid Fluorescence in Phosphatidylcholine Vesicles—A Probe for Membrane Organization," *Biophys. J.* 47:613-621, 1985.
Dai et al., "DNA-polyfluorophore excimers as sensitive reporters for esterases and lipases," *Chemical Communications* 46:1221-1223, 2010.
DiVittorio et al., "Synthetic peptides with selective affinity for apoptotic cells," *Organic & Biomolecular Chemistry* 4:1966-1976, 2006.
Gao et al., "Libraries of Composite Polyfluors Built from Fluorescent Deoxyribosides," *Jorunal of the American Chemical Society* 124:1590-11591, 2002.
Gao et al., "Modified DNA Analogues That Sense Light Exposure with Color Changes," *Journal of the American Chemical Society* 126:12748-12749, 2004.
Gordon et al., "Analysis of simulated and experimental fluorescence recovery after photobleaching. Data for two diffusing components," *Biophysical Journal* 68:766-778, 1995.
Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.
Haraguchi, "Live Cell Imaging: Approaches for Studying Protein Dynamics in Living Cells," *Cell Structure and Function* 27:333-334, 2002.
Koo et al., "Fluorescent DNA chemosensors: identification of bacterial species by their volatile metabolites," *Chemical Communications* 47:11435-11437, 2011.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.

Liu et al., "Detection of prostate-specific membrane antigen on HUVECs in response to breast tumor-conditioned medium," *International Journal of Oncology* 38:1349-1355, 2011.
Liu et al., "DNA-Based Micelles: Synthesis, Micellar Properties and Size-Dependent Cell Permeability," *Chem. Eur. J.* 16:3791-3797, 2010. (14 Pages).
Mersana Therapeutics, URL= http://www.mersana.com, download date Jan. 3, 2019, 9 pages.
Molotkovsky et al., "Perylenoyl- and Anthrylvinyl-Labeled Lipids as Membrane Probes," *Biochimica et Biophysica Acta* 778:281-288, 1984.
Nussbaumer et al., "Amplification of Chirality by Supramolecular Polymerization of Pyrene Oligomers," *Angewandte Chemie International Edition* 50:5490-5494, 2011.
Pownall et al., "Kinetics of Spontaneous and Plasma-Stimulated Sphingomyelin Transfer," *Biochimica et Biophysica Acta* 712:169-176, 1982.
PubChem, "US20100012929A1-20100121-C00010_4," SID No. 140452858, retrieved Mar. 29, 2016 from URL https://pubchem.ncbi.nlm.nih.gov/substance/140452858, 6 pages.
RN 230952-79-1, Registry Database Compound (1999).
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wilson et al., "Efficient Quenching of Oligomeric Fluorophores on a DNA Backbone," *Journal of the American Chemical Society* 129(50):15426-15427, 2007.
Wilson et al., "Oligodeoxyfluorosides: Strong Sequence of Dependence of Fluorescence Emission," *Tetrahedron* 63(17):3427-3433, 2007. (18 Pages).
Yurkovetskiy et al., "Advantages of Polyacetal Polymer-based Antibody Drug Conjugates: Application to Low Expression Targets," Mersana Therapeutics, technical paper #2645, 2014, 1 page.
U.S. Appl. No. 16/982,341, filed Sep. 18, 2020.
U.S. Appl. No. 16/982,355, filed Sep. 18, 2020.
U.S. Appl. No. 17/121,596, filed Dec. 14, 2020.
U.S. Appl. No. 17/255,353, filed Dec. 22, 2020.
Avirah et al., "Infrared Absorbing Croconaine Dyes: Synthesis and Metal Ion Binding Properties," *J. Org Chem.* 73(1):274-279, 2008.
Li et al., "Responsive nanogel-based dual fluorescent sensors for temperature and $Hg^{2+}$ ions with enhanced detection sensitivity," *J. Mater. Chem.* 20:10716-10723, 2010.
Stewart et al., "The Fluorescence of a Chelating Two-Photon-Absorbing Dye is Enhanced with the Addition of Transition Metal Ions but Quenched in the Presence of Acid," *Proc. of SPIE* 9939(993904):1-10, 2016.
Zhang et al., "FRET Imaging of Enzyme-Responsive HPMA Copolymer Conjugate," *Macromolecular Bioscience* 17(1600215):1-8, 2017.
Beaucage et al., "The Functionalization of Oligonucleotides via Phosphoramidite Derivatives," *Tetrahedron* 49(10):1925-1963, 1993.
Chattopadhyay et al., "Brilliant Violet Fluorophores: A New Class of Ultrabright Fluorescent Compounds for Immunofluorescence Experiments," *Cytometry Part A* 81A:456-466, 2012.
Cuppoletti et al., "Oligomeric fluorescent labels for DNA," *Bioconjug. Chem.* 16(3):528-534, 2005.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.
Dubrovsky, "Semiconductor nanoparticles as reporters in multiplexed immunoassay and cell analysis," *International Journal of Nanoscience* 8(1 & 2):163-167, 2009.
Jain et al. "Current ADC Linker Chemistry," *Pharm. Res.* 32:3526-3540, 2015.
Kozma et al., "Fluorescent Ligands for Adenosine Receptors," *Bioorganic & Medicinal Chemistry Letters* 23: 26-36, 2013.

(56) References Cited

OTHER PUBLICATIONS

Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.
Li et al., "Polymeric Drugs: Advances in the development of pharmacologically active polymers," *Journal of Controlled Release* 219:360-382, 2015.
Luo et al., "Sensitive and rapid quantification of C-reactive protein using quantum dot-labeled microplate immunoassay," *Journal of Translational Medicine* 10(24):1-9, 2012.
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.
Paris et al., "Probing DNA sequences in solution with a monomer-excimer fluorescence color change," *Nucleic Acids Research* 26(16):3789-3793, 1998.
Petreus et al., "Polyester imides containing main-chain phosphorus," *Revue Roumaine de Chimie* 34(8):971-978, 1994 (with English Abstract).
Ren et al., "An Antisense Oligodeoxynucleotide-Doxorubicin Conjugate: Preparation and Its Reversal Multidrug Resistance of Human Carcinoma Cell Line In Vitro," *Nucleosides, Nucleotides & Nucleic Acids* 23(10):1595-1607, 2004.
Singh et al., "Multiplexed measurement of membrane protein populations," *Caplus* 2003:769015, 2003. (2 pages).
Stuart et al., "Site-Specific DNA-Doxorubicin Conjugates Display Enhanced Cytotoxicity to Breast Cancer Cells," *Bioconjugate Chemistry* 25:406-413, 2014.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Tram et al., "Oligonucleotide Labeling Using BODIPY Phosphoramidite," *Nucleosides, Nucleotides & Nucleic Acids* 30(1):1-11, 2011.
Doi et al., "Hetero-Selective DNA-Like Duplex Stabilized by Donor-Acceptor Interactions," *Chem. Eur. J.* 21:15974-15980, 2015.
Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.
Johansson, "Choosing Reporter-Quencher Pairs for Efficient Quenching Through Formation of Intramolecular Dimers," *Methods in Molecular Biology* 335:17-29, 2006.
Masuko et al., "Fluorescence resonance energy transfer from pyrene to perylene labels for nucleic acid hybridization assays under homogenous solution conditions," *Nucleic Acids Research* 28(8):e34, 2000 (8 pages).
Saito et al., "Dual-labeled oligonucleotide probe for sensing adenosine via FRET: A novel alternative to SNPs genotyping," *Chem. Commun.*:2133-2135, 2007.
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.
Vinogradov et al., "Total synthesis and biochemical characterization of mirror image barnase," *Chem Sci.* 6: 2997-3002, 2015.
Aviñó et al., "Solid-phase synthesis of oligomers carrying several chromophore units linked by phosphodiester backbones," *Bioorganic & Medicinal Chemistry Letters* 18:2306-2310, 2008.
Boldyrev et al., "Synthesis and Characteristics of New Fluorescent Probes Based on Cardiolipin," *Russian Journal of Bioorganic Chemistry* 35(2):219-224, 2009.
Buckhout-White et al., "Assembling programmable FRET-based photonic networks using designer DNA scaffolds," *Nature Communications* 5:5615, Dec. 11, 2014. (16 pages).
CAS Registry No. 862288-26-4, American Chemical Society, 2021. (1 page).
De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.
Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.
Kashida et al., "A Cationic Dye Triplet as a Unique "Glue" That Can Connect Fully Matched Termini of DNA Duplexes," *Chem. Eur. J.* 17:2614-2622, 2011.
Lewis et al., "Orientation Control of Fluorescence Resonance Energy Transfer Using DNA as a Helical Scaffold," *J. Am. Chem. Soc.* 127(28):10002-10003, 2005.
Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.
Rochat et al., "Water-Soluble Cationic Conjugated Polymers: Response to Electron-Rich Bioanalytes," *J. Am. Chem. Soc.* 135:17703-17706, 2013.
Sun et al., "Dual-Color Fluorescence Imaging of Magnetic Nanoparticles in Live Cancer Cells Using Conjugated Polymer Probes," *Scientific Reports* 6:22368, 2016. (12 pages).
Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).
Vybornyi et al., "Formation of Two-Dimensional Supramolecular Polymers by Amphiphilic Pyrene Oligomers," *Angew. Chem. Int. Ed.* 52:114488-11493, 2013.
Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.
Winiger et al., "Long-Distance Electronic Energy Transfer in Light-Harvesting Supramolecular Polymers," *Angew. Chem. Int. Ed.* 53:13609-13613, 2014.
Zhao et al., "Mussel-Inspired One-Pot Synthesis of a Fluorescent and Water-Soluble Polydopamine-Polyethyleneimine Copolymer," *Macromol. Rapid Commun.* 36:909-915, 2015.

* cited by examiner

IONIC POLYMERS COMPRISING FLUORESCENT OR COLORED REPORTER GROUPS

BACKGROUND

Field

The present invention is generally directed to dimeric and polymeric fluorescent or colored dyes comprising charged spacing groups, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for water soluble dyes having an increased molar brightness. Ideally, such dyes and biomarkers should be intensely colored or fluorescent and should be available in a variety of colors and fluorescent wavelengths. The present invention fulfills this need and provides further related advantages.

BRIEF SUMMARY

In brief, embodiments of the present invention are generally directed to compounds useful as water soluble, fluorescent and/or colored dyes and/or probes that enable visual detection of analyte molecules, such as biomolecules, as well as reagents for their preparation. Methods for visually detecting analyte molecules using the dyes are also described.

Embodiments of the presently disclosed dyes include two or more fluorescent and/or colored moieties covalently linked by a linker. In contrast to previous reports of dimeric and/or polymeric dyes, the present dyes are significantly brighter than the corresponding monomeric dye compound. While, not wishing to be bound by theory, it is believed that the linker moiety provides sufficient spatial separation between the fluorescent and/or colored moieties such that intramolecular fluorescence quenching is reduced and/or eliminated.

The water soluble, fluorescent or colored dyes of embodiments of the invention are intensely colored and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In some embodiments, the required separation between the fluorescent and/or colored moieties is maintained by including two or more charged moieties within or pendant to the linker linking the fluorescent and/or colored moieties. While not wishing to be bound by theory, it is believed that repulsion of the charged moieties results in a more linear or "stretched" conformation for the polymers, thus maintaining sufficient spatial distance between the fluorescent and/or colored moieties to prevent or reduce intramolecular quenching.

Accordingly, in one embodiment is provided a polymer comprising:
 i) a backbone;
 ii) two or more charged moieties on the backbone; and
 iii) first and second colored or fluorescent moieties on the backbone, wherein the two or more charged moieties are in a position on the polymer backbone between the first and second colored or fluorescent moieties, and provided that at least one of the charged moieties is not phosphate. The disclosed polymers find utility in a number of applications, including use as fluorescent and/or colored dyes in various analytical methods.

In another embodiment, a method for staining a sample is provided, the method comprises adding to said sample a polymer as disclosed herein in an amount sufficient to produce an optical response when said sample is illuminated at an appropriate wavelength.

In still other embodiments, the present disclosure provides a method for visually detecting an analyte molecule, comprising:
 (a) providing a polymer as disclosed herein; and
 (b) detecting the polymer by its visible properties.

Other disclosed methods include a method for visually detecting a biomolecule, the method comprising:
 (a) admixing a polymer as disclosed herein with one or more biomolecules; and
 (b) detecting the polymer by its visible properties.

Other embodiments provide a method for visually detecting an analyte, the method comprising:
 (a) providing a compound as disclosed herein (e.g., structure (I)), wherein $R^2$ or $R^3$ comprises a linker comprising a covalent bond to a targeting moiety having specificity for the analyte;
 (b) admixing the compound and the analyte, thereby associating the targeting moiety and the analyte; and
 (c) detecting the compound by its visible properties.

Other embodiments are directed to a composition comprising a polymer disclosed herein (e.g., compound of structure (I)) and one or more analyte molecule, such as a biomolecule. Use of such compositions in analytical methods for detection of the one or more biomolecules is also provided.

Some other embodiments include a composition comprising a polymer disclosed herein (e.g., compound of structure (I)) and a cyclodextrin.

Other embodiments are directed to a composition comprising a polymer as disclosed herein and one or more biomolecules. Use of such compositions in analytical methods for detection of the one or more biomolecules is also provided.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the $-NH_2$ group.
"Carboxy" refers to the $-CO_2H$ group.
"Cyano" refers to the $-CN$ group.
"Formyl" refers to the $-C(=O)H$ group.
"Hydroxy" or "hydroxyl" refers to the $-OH$ group.
"Imino" refers to the $=NH$ group.
"Nitro" refers to the $-NO_2$ group.
"Oxo" refers to the $=O$ substituent group.
"Sulfate" refers to the $-OS(=O)_2O^-$ group.
"Sulfhydryl" refers to the $-SH$ group.
"Thioxo" refers to the $=S$ group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or $-OP(=R_a)(R_b)R_c$, wherein each of $R_a$, $R_b$ and $R_c$ is as defined for compounds of structure (I).

"Alkoxy" refers to a group of the formula $-OR_a$ where $R_a$ is an alkyl group as defined above containing one to twelve carbon atoms. Unless stated otherwise specifically in the specification, an alkoxy group is optionally substituted.

"Alkoxyalkylether" refers to a group of the formula $-OR_aR_b$ where $R_a$ is an alkylene group as defined above containing one to twelve carbon atoms, and Rb is an alkylether group as defined herein. Unless stated otherwise specifically in the specification, an alkoxyalkylether group is optionally substituted, for example substituted with an alcohol or $-OP(=R_a)(R_b)R_c$, wherein each of $R_a$, $R_b$ and $R_c$ is as defined for compounds of structure (I).

"Heteroalkoxy" refers to a group of the formula $-OR_a$ where $R_a$ is a heteroalkyl group as defined above containing one to twelve carbon atoms. Unless stated otherwise specifically in the specification, a heteroalkoxy group is optionally substituted.

"Heteroalkyl" refers to an alkyl group, as defined above, comprising at least one heteroatom (e.g., N, O, P or S) within the alkyl chain or at a terminus of the alkylene chain. In some embodiments, the heteroatom is within the alkyl chain (i.e., the heteroalkyl comprises at least one carbon-heteroatom bond). In other embodiments, the heteroatom is at a terminus of the alkyl group. Heteroatom substitutions include phosphate and amine groups (including protonated and quaternary). Unless stated otherwise specifically in the specification, a heteroalkyl group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]$_x$-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene linking group include ethylene oxide (e.g., PEG) linkers and the linker illustrated below:

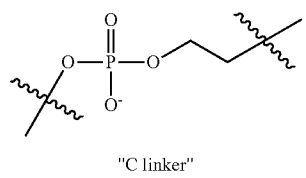 [SMILES: *CCOP(=O)([O-])O*]

"C linker"

Multimers of the above C-linker are included in various embodiments of heteroalkylene linkers.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O⁻)(=O)O— or —OP(O⁻)(=O)O— and multimers and combinations thereof.

"Phosphate" refers to the —OP(=O)(R$_a$)R$_b$ group, wherein R$_a$ is OH, O⁻ or OR$_c$; and R$_b$ is OH, O⁻, OR$_c$, a thiophosphate group or a further phosphate group, wherein R$_c$ is a counter ion (e.g., Na+ and the like).

"Phosphoalkyl" refers to the —OP(=O)(R$_a$)R$_b$ group, wherein R$_a$ is OH, O⁻ or OR$_c$; and R$_b$ is —Oalkyl, wherein R$_c$ is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Phosphoalkylether" refers to the —OP(=O)(R$_a$)R$_b$ group, wherein R$_a$ is OH, O⁻ or OR$_c$; and R$_b$ is —Oalkylether, wherein R$_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether or thiophosphoalkylether or —OP(=R$_a$)(R$_b$)R$_c$, wherein each of R$_a$, R$_b$ and R$_c$ is as defined for compounds of structure (I).

"Thiophosphate" refers to the —OP(=R$_a$)(R$_b$)R$_c$ group, wherein R$_a$ is O or S, R$_b$ is OH, O⁻, S⁻, OR$_d$ or SR$_d$; and R$_c$ is OH, SH, O⁻, S⁻, OR$_d$, SR$_d$, a phosphate group or a further thiophosphate group, wherein R$_d$ is a counter ion (e.g., Na+ and the like) and provided that: i) R$_a$ is S; ii) R$_b$ is S⁻ or SR$_d$; iii) R$_c$ is SH, S⁻ or SR$_d$; or iv) a combination of i), ii) and/or iii).

"Thiophosphoalkyl" refers to the —OP(=R$_a$)(R$_b$)R$_c$ group, wherein R$_a$ is O or S, R$_b$ is OH, O⁻, S⁻, OR$_d$ or SR$_d$; and R$_c$ is —Oalkyl, wherein R$_d$ is a counter ion (e.g., Na+ and the like) and provided that: i) R$_a$ is S; ii) R$_b$ is S⁻ or SR$_d$; or iii) R$_a$ is S and R$_b$ is S⁻ or SR$_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Thiophosphoalkylether" refers to the —OP(=R$_a$)(R$_b$)R$_c$ group, wherein R$_a$ is O or S, R$_b$ is OH, O⁻, S⁻, OR$_d$ or SR$_d$; and R$_c$ is —Oalkylether, wherein R$_d$ is a counter ion (e.g., Na+ and the like) and provided that: i) R$_a$ is S; ii) R$_b$ is S⁻ or SR$_d$; or iii) R$_a$ is S and R$_b$ is S⁻ or SR$_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is —OP(=R$_a$)(R$_b$)R$_c$, wherein each of R$_a$, R$_b$ and R$_c$ is as defined for compounds of structure (I). In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1, 3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (e.g., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (e.g., the polymers having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000$M^{-1}$ $cm^{-1}$. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the polymer disclosed herein linked to a biomolecule; and (b) detecting the biomolecule by its visible properties. For purposes of embodiments of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass all of the disclosed polymers being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively.

Isotopically-labeled polymers can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethane-sulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds or polymers described herein. Embodiments of the present invention include all solvates of the described polymers and compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The polymers and compounds of the invention may be true solvates, while in other cases the compounds of the invention may merely retain adventitious water or another solvent or be a mixture of water plus some adventitious solvent.

Embodiments of the compounds of the invention (also referred to herein as polymers), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of the disclosed polymers. Various tautomeric forms of the polymers are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, polymers useful as fluorescent and/or colored dyes in various analytical methods are provided. In general terms, embodiments of the present invention are directed to dimers and higher polymers of fluorescent and/or colored moieties. The fluorescent and or colored moieties are linked by a linking moiety (e.g., a portion of the polymer backbone) comprising one or more charged moiety, for example at least two charged moieties. Without wishing to be bound by theory, it is believed that the presence of charge in the linker helps to maintain sufficient spatial distance between the fluorescent and/or colored moieties such that intramolecular quenching is reduced or eliminated, thus resulting in a dye compound having a high molar "brightness" (e.g., high fluorescence emission).

Accordingly, in some embodiments is provided a polymer comprising:

i) a backbone;
ii) two or more charged moieties on the backbone; and
iii) first and second colored or fluorescent moieties on the backbone, wherein the two or more charged moieties are in a position on the polymer backbone between the first and second colored or fluorescent moieties, and provided that at least one of the charged moieties is not phosphate. In other embodiments at least one of the charged moieties is not an amino acid, for example in some embodiments the polymers do not include peptide-like backbones.

In some embodiments, the charged moieties are positively charged. For example, in some embodiments the charged moieties comprise a protonated amine or quaternary amine functional group.

In other embodiments, the charged moieties are negatively charged. For example, in some embodiments the charged moieties comprise a carboxylic acid or sulfate functional group.

The charged moieties may be included in the polymer in a variety of different manners. For example, in some embodiments the charged moieties are within the polymer backbone (i.e., part of the polymer backbone). In other embodiments, the charged moieties are covalently bound pendent to the backbone via an optional linker.

The polymer backbone can be formed from any type of monomer, and include all the same monomers (homopolymer) or a mixture of different monomers (copolymer). In some embodiments, the backbone comprises a backbone resulting from polymerization of: a phopshoramidite and an alcohol; an amine and an epoxide; an amine and an aldehyde; N-carboxyanhydride, or a combination thereof.

In other embodiments, the backbone comprises a polyamide, a polyamine, dextrin, dextran, cellulose, chitosan, polyacrylate, polysulfate or polycarboxylic acid.

In some embodiments, the polymer has the following structure (I):

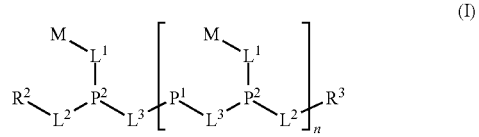

or a stereoisomer, salt or tautomer thereof, wherein:

M is, at each occurrence, independently the fluorescent or colored moiety;

$P^1$ is, at each occurrence, independently a section of the backbone comprising the two charged moieties;

$P^2$ is, at each occurrence, independently a section of the backbone to which the fluorescent or colored moiety is attached;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ is at each occurrence, independently absent, a section of the backbone or a linker linking $P^2$ to $R^2$ or $P^2$ to $R^3$;

$L^3$ is, at each occurrence, independently an optional linker linking $P^1$ to $P^2$;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or L';

$R_a$ is O or S;

$R_b$ is OH, SH, O$^-$, S$^-$, OR$_d$ or SR$_d$;

$R_c$ is OH, SH, O$^-$, S$^-$, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I); and n is an integer of one or greater.

In other embodiments of structure (I):

M is, at each occurrence, independently the fluorescent or colored moiety;

$P^1$ is, at each occurrence, independently a section of the backbone comprising the two charged moieties;

$P^2$ is, at each occurrence, independently a section of the backbone to which the fluorescent or colored moiety is attached;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ is at each occurrence, independently absent, a section of the backbone or a linker linking $P^2$ to $R^2$ or $P^2$ to $R^3$;

$L^3$ is, at each occurrence, independently an optional linker linking $P^1$ to $P^2$;

$R^1$ is, at each occurrence, independently H, alkyl or alkoxy;

$R^2$ and $R^3$ are each independently a polymer terminal group, H, OH, SH, amino, alkylaminyl, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, O$^-$, S$^-$, OR$_d$ or SR$_d$; $R_c$ is OH, SH, O$^-$, S$^-$, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether; and is a $C_1$-$C_6$ alkyl or a counter ion;

Q is, at each occurrence, independently a moiety comprising a reactive group capable of forming a covalent bond with an analyte molecule, a solid support or a complementary reactive group Q'; and n is an integer of one or greater.

The various linkers, substituents and backbone sections (e.g., M, Q, R, $R^2$, $R^3$, L', $L^1$, $L^2$, $L^3$, $P^1$ and $P^2$) in the polymer are optionally substituted with one more substituent. For example, in some embodiments the optional substituent is selected to optimize the water solubility or other property of the polymer. In certain embodiments, each alkyl, alkoxy, alkylether, alkoxyalkylether, phosphoalkyl, thiophosphoalkyl, phosphoalkylether and thiophosphoalkylether in the polymer is optionally substituted with one more substituent selected from the group consisting of heteroalkyl, hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments the optional substituent is —OP(=$R_a$)($R_b$)$R_c$, where $R_a$, $R_b$ and $R_c$ are as defined for the compound of structure (I).

In some embodiments, $P^1$ has one of the following structures:

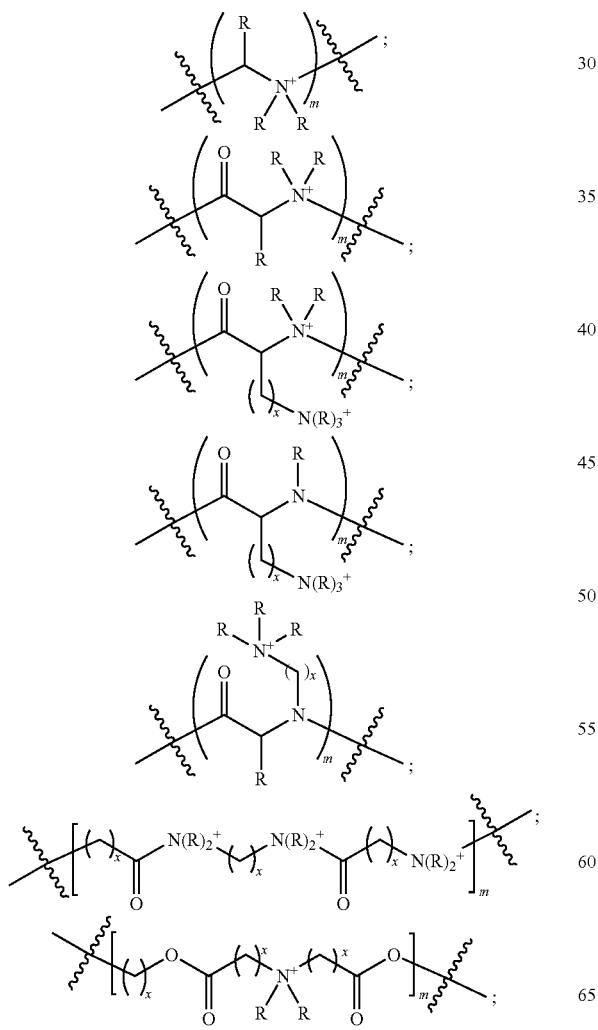

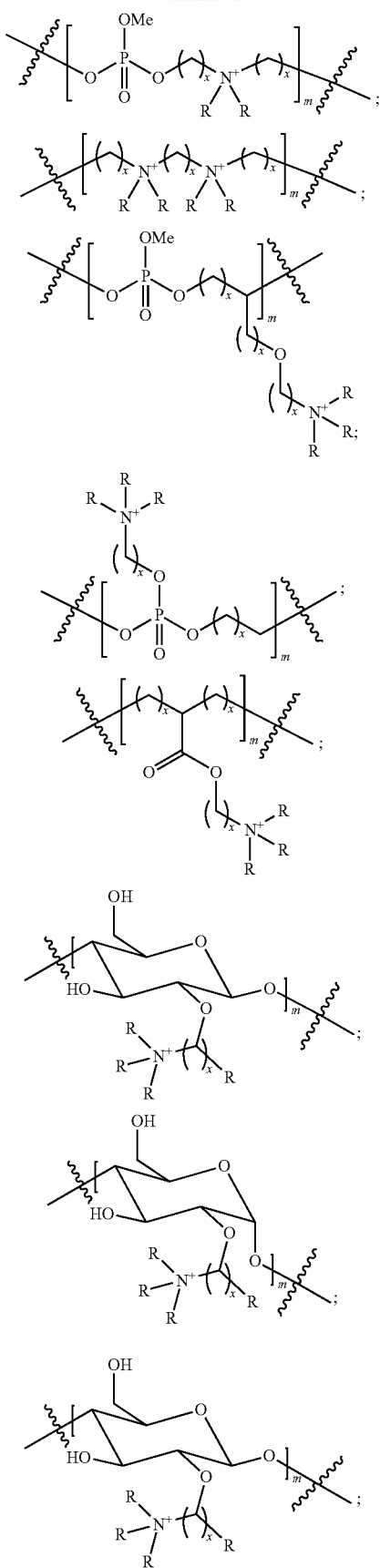

-continued

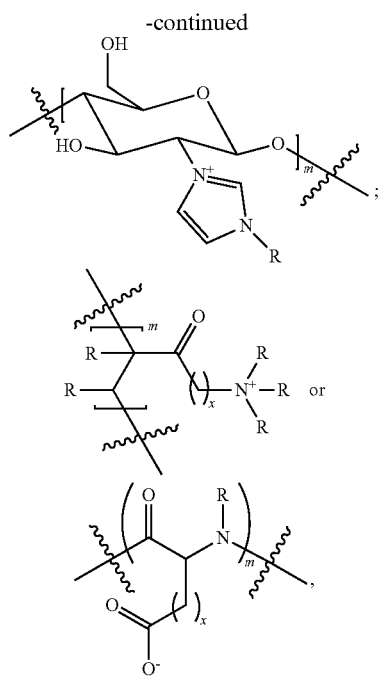

wherein:
R is H or $C_1$-$C_6$ alkyl;
x is an integer from 0 to 6; and
m is an integer of 1 or greater, provided that m is selected such that $P^1$ comprises at least two charged moieties.

The optional linker $L^1$ can be used as a point of attachment of the M moiety to the remainder of the compound. For example, in some embodiments a synthetic precursor of the polymer is prepared, and the M moiety is attached to the synthetic precursor using any number of facile methods known in the art, for example methods referred to as "click chemistry." For this purpose any reaction which is rapid and substantially irreversible can be used to attach M to the synthetic precursor to form the final polymer. Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothioscyanate or the like. In some embodiments the reaction to form $L^1$ may be performed in an aqueous environment.

Accordingly, in some embodiments $L^1$ is at each occurrence a linker comprising a functional group capable of formation by reaction of two complementary reactive groups, for example a functional group which is the product of one of the foregoing "click" reactions. In various embodiments, for at least one occurrence of $L^1$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group. For example, reaction of an amine with an N-hydroxysuccinimide ester or isothiocyanate.

In other embodiments, for at least one occurrence of $L^1$, the functional group can be formed by reaction of an alkyne and an azide. In other embodiments, for at least one occurrence of $L^1$, the functional group can be formed by reaction of an amine (e.g., primary amine) and an N-hydroxysuccinimide ester or isothiocyanate.

In more embodiments, for at least one occurrence of $L^1$, the functional group comprises an alkene, ester, amide, thioester, disulfide, carbocyclic, heterocyclic or heteroaryl group. In more embodiments, for at least one occurrence of $L^1$, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of $L^1$, $L^1$ is a linker comprising a triazolyl functional group. While in other embodiments, for at least one occurrence of $L^1$, $L^1$ is a linker comprising an amide or thiourea functional group.

In still other embodiments, for at least one occurrence of $L^1$, $L^1$-M has the following structure:

wherein $L^{1a}$ and $L^{1b}$ are each independently optional linkers.

In different embodiments, for at least one occurrence of $L^1$, $L^1$-M has the following structure:

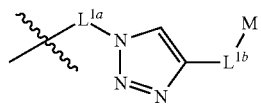

wherein $L^{1a}$ and $L^{1b}$ are each independently optional linkers.

In various embodiments of the foregoing, $L^{1a}$ or $L^{1b}$, or both, is absent. In other embodiments, $L^{1a}$ or $L^{1b}$, or both, is present.

In still other different embodiments of structure (I), $L^1$ is at each occurrence, independently an optional alkylene or heteroalkylene linker.

In more embodiments, $L^2$ and $L^3$ are, at each occurrence, independently $C_1$-$C_6$ alkylene, $C_2$-$C_6$ alkenylene or $C_2$-$C_6$ alkynylene.

In other various embodiments, $R^2$ and $R^3$ are each independently OH or —OP(=$R_a$)($R_b$)$R_c$. In some different embodiments, $R^2$ or $R^3$ is OH or —OP(=$R_a$)($R_b$)$R_c$, and the other of $R^2$ or $R^3$ is Q or a linker comprising a covalent bond to Q.

In still more different embodiments of any of the foregoing compounds of structure (I), $R^2$ and $R^3$ are each independently —OP(=$R_a$)($R_b$)$R_c$. In some of these embodiments, $R_c$ is OL'.

In other embodiments, $R^2$ and $R^3$ are each independently —OP(=$R_a$)($R_b$)OL', and L' is an alkylene or heteroalkylene linker to: Q, a targeting moiety, an analyte (e.g., analyte molecule), a solid support, a solid support residue, a nucleoside or a further compound of structure (I).

The linker L' can be any linker suitable for attaching Q, a targeting moiety, an analyte (e.g., analyte molecule), a solid support, a solid support residue, a nucleoside or a further compound of structure (I) to the compound of structure (I). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

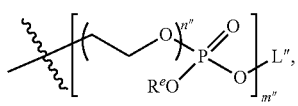

wherein:

m" and n" are independently an integer from 1 to 10;

$R^e$ is H, an electron pair or a counter ion;

L" is $R^e$ or a direct bond or linkage to: Q, a targeting moiety, an analyte (e.g., analyte molecule), a solid support, a solid support residue, a nucleoside or a further compound of structure (I).

In some embodiments, m" is an integer from 4 to 10, for example 4, 6 or 10. In other embodiments n" is an integer from 3 to 6, for example 3, 4, 5 or 6.

In some other embodiments, L" is an alkylene or heteroalkylene moiety. In some other certain embodiments, L" comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In other more specific embodiments of any of the foregoing compounds of structure (I), $R^2$ or $R^3$ has one of the following structures:

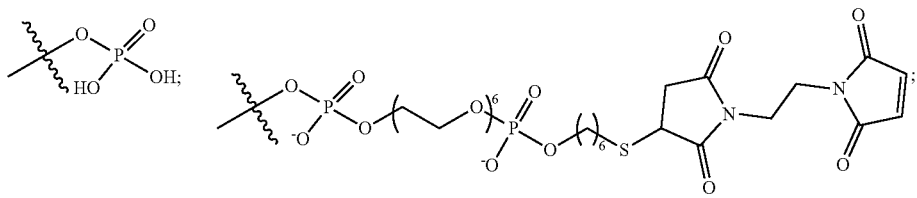

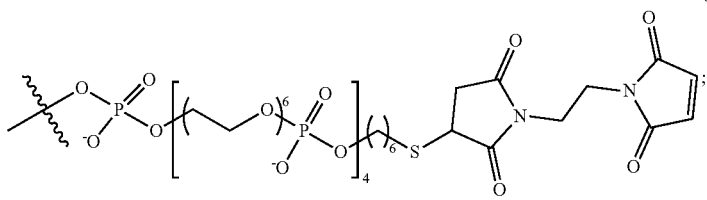

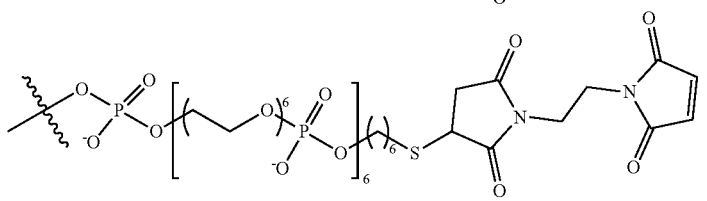

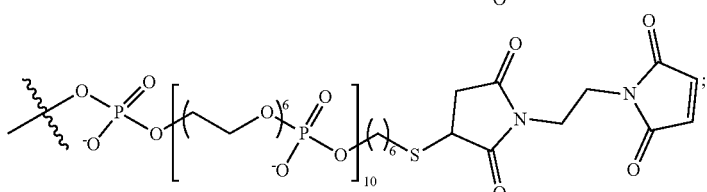

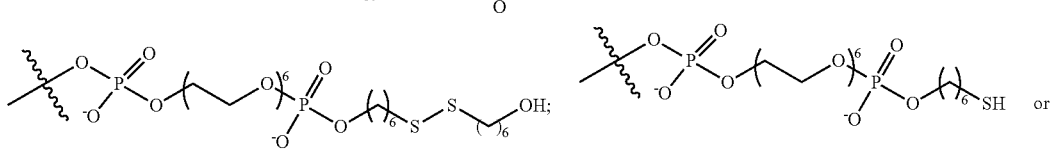

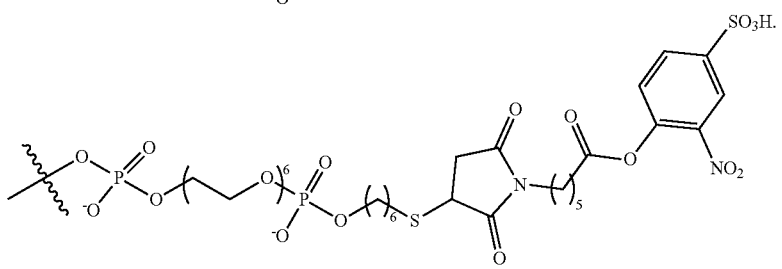

Certain embodiments of compounds of structure (I) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (I). Accordingly, in some embodiments $R^2$ or $R^3$ has the following structure:

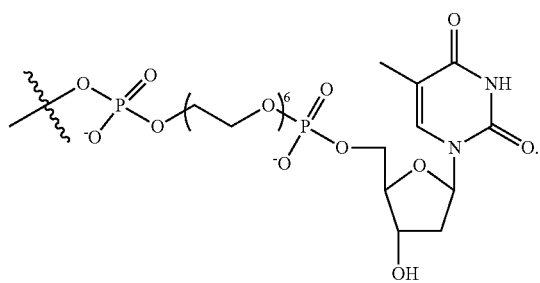

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further polymer (e.g., in the $R^2$ or $R^3$ position of structure (I)), and Q and Q' comprise complementary reactive groups such that reaction of the polymer and the further polymer results in covalently bound dimer of the polymer. Multimer polymers can also be prepared in an analogous manner and are included within the scope of embodiments of the invention.

The type of Q group and connectivity of the Q group to the remainder of the polymer is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of the polymers comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

In other embodiments, the Q moiety is conveniently masked (e.g., protected) as a disulfide moiety, which can later be reduced to provide an activated Q moiety for binding to a desired analyte molecule or targeting moiety. For example, the Q moiety may be masked as a disulfide having the following structure:

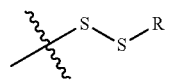

wherein R is an optionally substituted alkyl group. For example, in some embodiments, Q is provided as a disulfide moiety having the following structure:

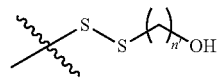

where n is an integer from 1 to 10, for example 6.

Exemplary Q moieties are provided in Table I below.

TABLE 1

Exemplary Q Moieties

| Structure | Class |
| --- | --- |
| —SH | Sulfhydryl |
| —N=C=S | Isothiocyanate |
| (structure with O, NH$_2^+$Cl$^-$) | Imidoester |
| (structure with C=O, N=N$^+$=N$^-$) | Acyl Azide |

TABLE 1-continued

Exemplary Q Moieties

| Structure | Class |
|---|---|
| (tetrafluorophenyl ester) | Activated Ester |
| (pentafluorophenyl ester) | Activated Ester |
| (4-sulfo-2-nitrophenyl ester) | Activated Ester |
| (thiosuccinimide-linked sulfo-nitrophenyl ester) | Activated Ester |
| (N-hydroxysuccinimide ester) | Activated Ester |
| (sulfo-N-hydroxysuccinimide ester) | Activated Ester |
| (sulfonyl halide), X = halo | Sulfonyl halide |
| (maleimide) | Maleimide |
| (thiosuccinimide-ethyl-maleimide) | Maleimide |
| (cyclohexyl-maleimide amide) | Maleimide |
| (haloacetamide), X = halo | α-haloimide |
| (pyridyl disulfide) | Disulfide |
| (phosphine ester) | Phosphine |
| (azide) | Azide |
| (alkyne) | Alkyne |
| (biotin) | Biotin |
| (diene) | Diene |

TABLE 1-continued

Exemplary Q Moieties

| Structure | Class |
|---|---|
| 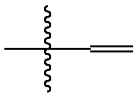 | Alkene/dienophile |
| 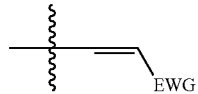 EWG = electron withdrawing group | Alkene/dienophile |
| —NH$_2$ | Amino |

It should be noted that in some embodiments, wherein Q is SH, the SH moiety will tend to form disulfide bonds with another sulfhydryl group on another polymer. Accordingly, some embodiments include polymers, which are in the form of disulfide dimers, the disulfide bond being derived from SH Q groups.

In some other embodiments, one of $R^2$ or $R^3$ is OH or —OP(=$R_a$)($R_b$)$R_c$, and the other of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

The fluorescence intensity can also be tuned by selection of different values of n. In certain embodiments, n is an integer from 1 to 100. In other embodiments, n is an integer from 1 to 10.

The fluorescent or colored moiety ("M") is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. For example, in some embodiments each M is not the same and the different M moieties are selected to have absorbance and/or emissions for use in fluorescence resonance energy transfer (FRET) methods. For example, in such embodiments the different M moieties are selected such that absorbance of radiation at one wavelength causes emission of radiation at a different wavelength by a FRET mechanism. Exemplary M moieties can be appropriately selected by one of ordinary skill in the art based on the desired end use. Exemplary M moieties for FRET methods include fluorescein and 5-TAMRA (5-carboxytetramethylrhodamine, succinimidyl ester) dyes.

M may be attached to the remainder of the molecule from any position (i.e., atom) on M. One of skill in the art will recognize means for attaching M to the remainder of molecule. Exemplary methods include the "click" reactions described herein.

In some embodiments, M is a fluorescent or colored moiety. Any fluorescent and/or colored moiety may be used, for examples those known in the art and typically employed in colorimetric, UV, and/or fluorescent assays may be used. Examples of M moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing polymers, such as polymers of structure (I), M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, M is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrromethaneboron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or derivative thereof. In some other embodiments, M has one of the following structures:

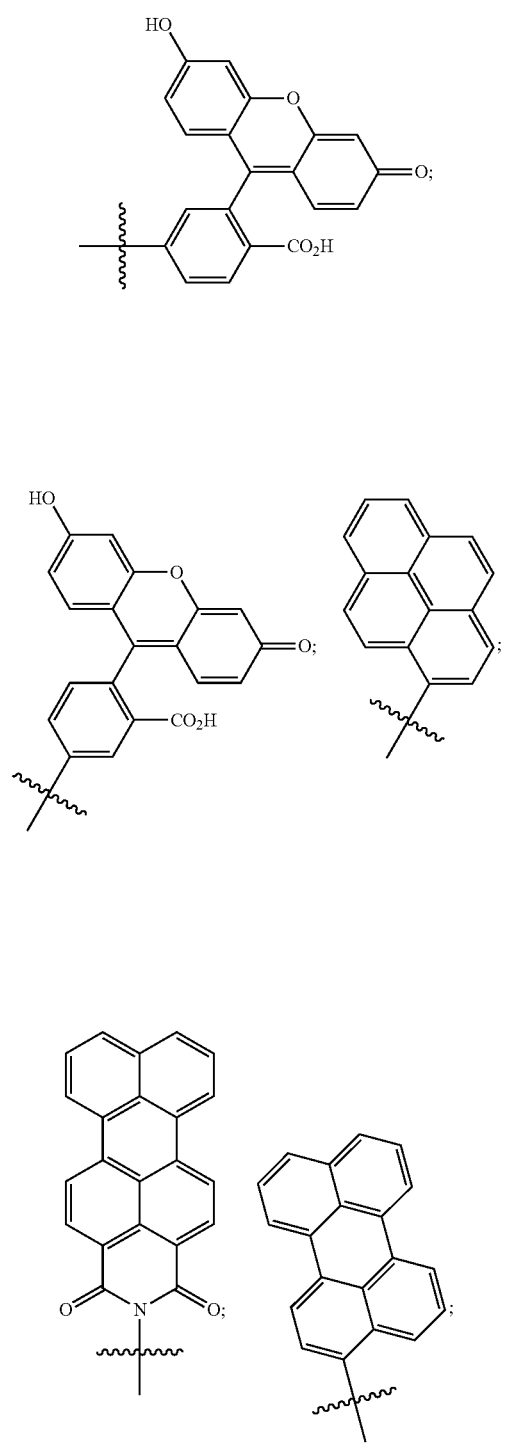

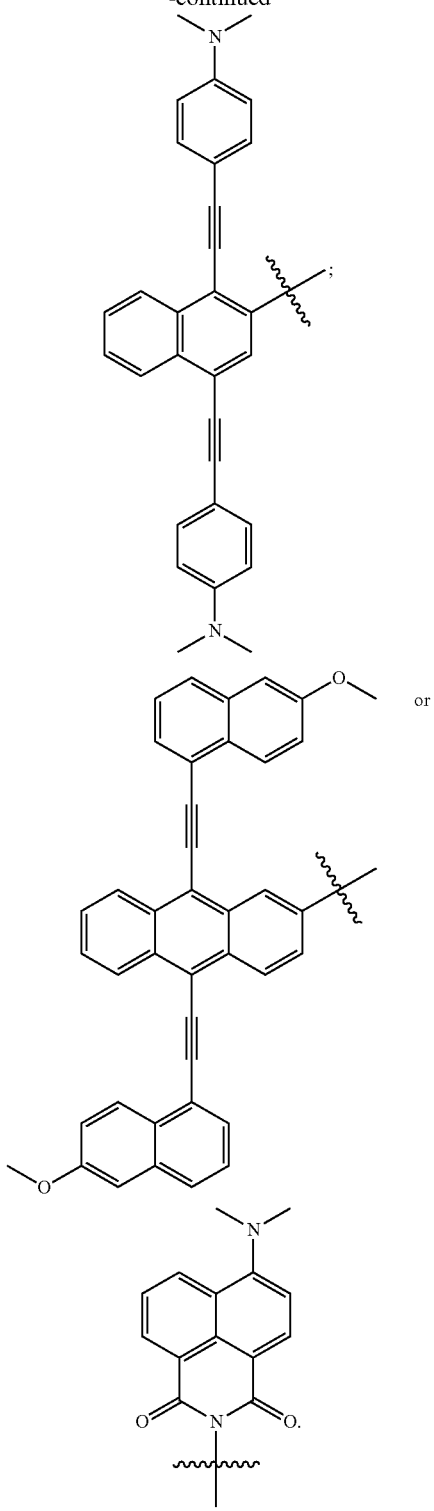

Although M moieties comprising carboxylic acid groups are depicted in the anionic form ($CO_2^-$) above, one of skill in the art will understand that this will vary depending on pH, and the protonated form ($CO_2H$) is included in various embodiments.

In some specific embodiments, the polymer is a polymer selected from Table 2.

TABLE 2

Exemplary Polymers

| No. | Structure |
|---|---|
| I-1 | 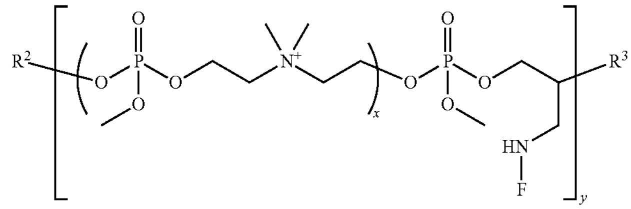 |
| I-2 | 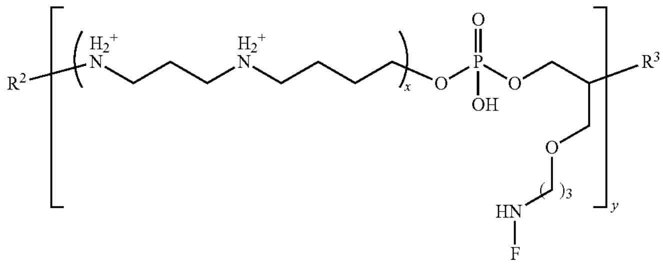 |
| I-3 | 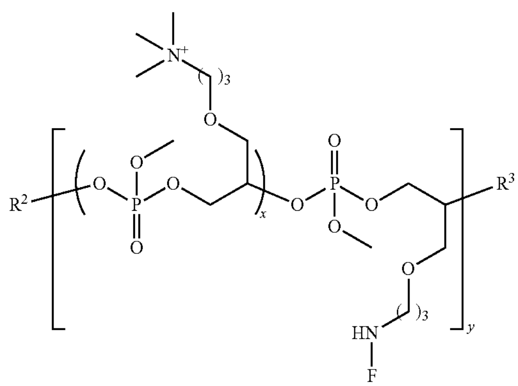 |
| I-4 | 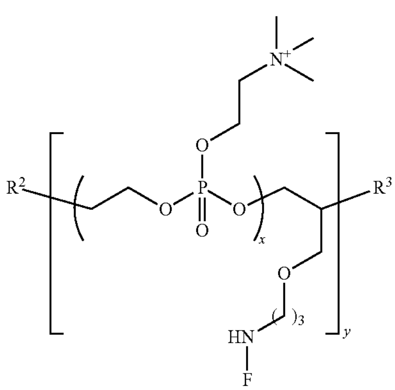 |
| I-5 | 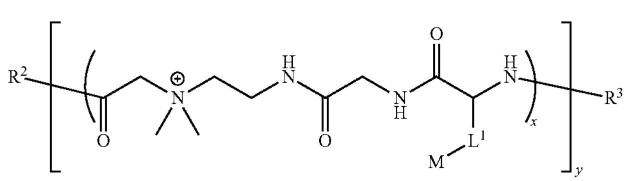 |

TABLE 2-continued
Exemplary Polymers
| No. | Structure |
|---|---|
| I-6 | 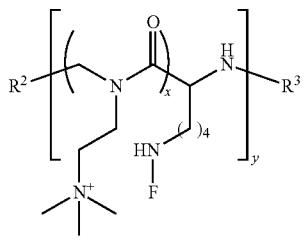 |
| I-7 | 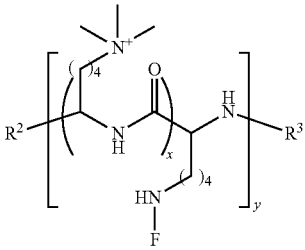 |
| I-8 | 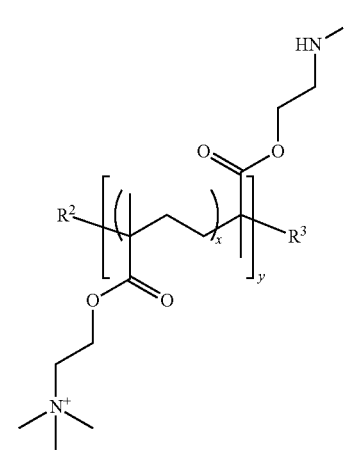 |
| I-9 | 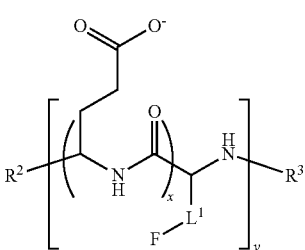 |
In some embodiments, the polymers do not include the following polymer:
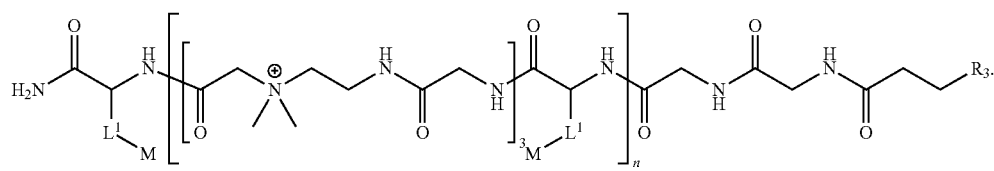

As used in Table 2: x is, at each occurrence, independently an integer of 1 or greater, provided that x is selected such that the compound includes at least two charged moieties for at least one integral value of y; y is an integer of 2 or greater; $R^2$, $R^3$ and $L^1$ are as defined herein; and F refers to a fluorescein moiety have the following structure:

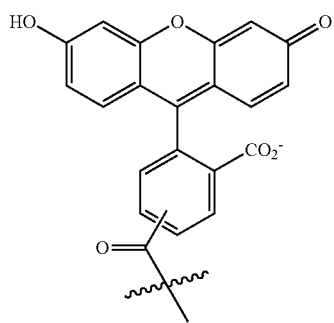

The presently disclosed dye polymers are "tunable," meaning that by proper selection of the variables in any of the foregoing compounds, one of skill in the art can arrive at a polymer having a desired and/or predetermined molar fluorescence (molar brightness). The tunability of the polymers allows the user to easily arrive at polymers having the desired fluorescence and/or color for use in a particular assay or for identifying a specific analyte of interest. Although all variables may have an effect on the molar fluorescence of the polymers, proper selection of M, $P^1$ and n is believed to play an important role in the molar fluorescence of the polymers. Accordingly, in one embodiment is provided a method for obtaining a polymer having a desired molar fluorescence, the method comprising selecting an M moiety having a known fluorescence, preparing a polymer comprising the M moiety, and selecting the appropriate variables for $P^1$ and n to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9× 10× or even higher relative to the parent fluorophore. Various embodiments include preparing compounds having the desired fold increase in fluorescence relative to the parent fluorophore by proper selection of $P^1$, M and n.

For ease of illustration, various compounds comprising phosphorous moieties (e.g., phosphate and the like) are depicted in the anionic state (e.g., —OPO(OH)O⁻, —OPO₃²⁻). One of skill in the art will readily understand that the charge is dependent on pH and the uncharged (e.g., protonated or salt, such as sodium or other cation) forms are also included in the scope of embodiments of the invention.

In some embodiments, any of the foregoing polymers (e.g., structure (I)) are included in a composition further comprising one or more cyclodextrin. Without wishing to be bound by theory, it is believed the cyclodextrin helps to prevent or reduce intramolecular quenching of the dye moieties (e.g., fluorescent and/or colored moieties), thus resulting in a dye compound having a high molar "brightness" (e.g., high fluorescence emission).

Any cyclodextrin may be employed in practice of various embodiments, provided the cyclodextrins reduces or prevents intramolecular quenching of the dye moieties. Typically a cyclodextrin having affinity for the polymer are selected. In some embodiments, the cyclodextrin is α-cyclodextrin, β-cyclodextrin or γ-cyclodextrin. For example, in some embodiments the cyclodextrin is β-cyclodextrin. In some embodiments, such compositions comprise water.

Compositions comprising any of the foregoing polymers and one or more analyte molecules (e.g., biomolecules) are provided in various other embodiments. In some embodiments, use of such compositions in analytical methods for detection of the one or more analyte molecules are also provided.

In still other embodiments, the polymers are useful in various analytical methods. For example, in certain embodiments the disclosure provides a method of staining a sample, the method comprising adding to said sample a polymer as disclosed herein in an amount sufficient to produce an optical response when said sample is illuminated at an appropriate wavelength. For example, in certain embodiments of such methods the polymer is a compound of has structure (I), for example wherein one of $R^2$ or $R^3$ is a linker comprising a covalent bond to an analyte molecule (e.g., biomolecule) or microparticle, and the other of $R^2$ or $R^3$ is H, OH, alkyl, alkoxy, alkylether or —OP(=$R_a$)($R_b$)$R_c$, in an amount sufficient to produce an optical response when said sample is illuminated at an appropriate wavelength.

In some embodiments of the foregoing methods, $R^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:

(a) providing a polymer as disclosed herein, wherein the polymer comprises a covalent bond to the analyte molecule; and (b) detecting the polymer by its visible properties.

For example, in some embodiments the disclosure provides a method for visually detecting an analyte molecule, such as a biomolecule, comprising:

(a) providing a polymer having structure (I), for example, wherein one of $R^2$ or $R^3$ is a linker comprising a covalent bond to the analyte molecule, and the other of $R^2$ or $R^3$ is H, OH, alkyl, alkoxy, alkylether or —OP($=R_a$)($R_b$)$R_c$; and (b) detecting the polymer by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:

(a) admixing any of the foregoing polymers with one or more analyte molecules; and (b) detecting the polymer by its visible properties.

In other embodiments is provided a method for visually detecting an analyte molecule, the method comprising:

(a) admixing a polymer disclosed herein, wherein the polymer comprises a Q group, with the analyte molecule;

(b) forming a conjugate of the polymer and the analyte molecule by reaction of the Q group with a complementary group on the analyte molecule; and (c) detecting the conjugate by its visible properties.

For example, in some embodiments is provided a method for visually detecting an analyte molecule, the method comprising:

(a) admixing a polymer having structure (I), wherein $R^2$ or $R^3$ is Q or a linker comprising a covalent bond to Q, with the analyte molecule;

(b) forming a conjugate of the compound and the analyte molecule by reaction of the Q group with a complementary group on the analyte molecule; and (c) detecting the conjugate by its visible properties.

Other exemplary methods include a method for detecting an analyte, the method comprising:

(a) providing a compound of structure (I), wherein $R^2$ or $R^3$ comprises a linker comprising a covalent bond to a targeting moiety having specificity for the analyte;

(b) admixing the compound and the analyte, thereby associating the targeting moiety and the analyte; and (c) detecting the compound, for example by its visible or fluorescent properties.

In certain embodiments of the foregoing method, the analyte is a particle, such as a cell, and the method includes use of flow cytometry. For example, the compound may be provided with a targeting moiety, such as an antibody, for selectively associating with the desired cell, thus rendering the cell detectable by any number of techniques, such as visible or fluorescence detection. Appropriate antibodies can be selected by one of ordinary skill in the art depending on the desired end use. Exemplary antibodies for use in certain embodiments include UCHT1 and MOPC-21.

Embodiments of the present compounds thus find utility in any number of methods, including, but not limited: cell counting; cell sorting; biomarker detection; quantifying apoptosis; determining cell viability; identifying cell surface antigens; determining total DNA and/or RNA content; identifying specific nucleic acid sequences (e.g., as a nucleic acid probe); and diagnosing diseases, such as blood cancers.

In addition to the above methods, embodiments of the polymers disclosed herein find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by conjugating a polymer disclosed herein to an antibody or sugar or other moiety that preferentially binds cancer cells; imaging in surgical procedures; binding of histones for identification of various diseases; drug delivery, for example by replacing the M moiety in a polymer disclosed herein with an active drug moiety; and/or contrast agents in dental work and other procedures, for example by preferential binding of a polymer disclosed herein to various flora and/or organisms.

It is understood that any embodiment of the polymers of structure (I), as set forth above, and any specific choice set forth herein for a $R^2$, $R^3$, L', $L^1$, $L^2$, $L^3$, $P^1$, $P^2$, Q, Q', M, m and/or n variable in the polymers of structure (I), as set forth above, may be independently combined with other embodiments and/or variables of the polymers of structure (I) to form embodiments of the invention not specifically set forth above. In addition, in the event that a list of choices is listed for any particular $R^2$, $R^3$, L', $L^1$, $L^2$, $L^3$, $P^1$, $P^2$, Q, Q', M, m and/or n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Examples illustrate exemplary methods of making the polymers disclosed herein. It is understood that one skilled in the art may be able to make these polymers by similar methods or by combining other methods known to one skilled in the art. It is also understood that one skilled in the art would be able to make, in a similar manner as described below, other polymers not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

In general, the polymers described herein can be prepared according to techniques known in the art, for example by polymerization of monomers using known techniques, such as solid-phase DNA or peptide synthesis. The charged moieties can be incorporated into the polymers as monomers, or the polymer itself can be modified to include the charged moieties, for example by reaction of an amine-containing polymer with an alkyl halide (e.g., methyl bromide) or acid. Similarly, the fluorescent and/or colored moieties can be incorporated as monomers or by modification of the polymer. For example, reactive moieties such as amines or carboxylic acids on the polymer can be used as a point of attachment of for a fluorescent or colored moiety comprising a complementary group (e.g., by formation of an amide bond).

Alternatively, polymers are prepared comprising an appropriate "click" functional group and fluorescent or colored moieties comprising a complementary "click" functional group are covalently bound to the polymer using "click" chemistry as known in the art. Click chemistry refers to any reaction which is rapid and substantially irreversible. Click functional groups refer to functional groups which react to form a covalent bond under click chemistry conditions. Exemplary click reactions and functional groups include the copper catalyzed reaction of an azide and alkyne to form a triazolyl (Huises 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. In some embodiments the click reaction may be performed in an aqueous environment.

In some embodiments, the polymer is prepared by polymerization of: a phosphoramidite and an alcohol; an amine and an epoxide; an amine and an aldehyde; or N-carboxyanhydride. The charged and/or fluorescent and/or colored moieties are present in the pre-polymerized monomers or added post polymerization as described above. In some embodiments, commercially available polymers, such as cellulose, dextrin, dextran chitosan or gelatin polymers are modified to include the charged moieties and/or the fluorescent and/or colored moieties.

For preparation of polymers by solid-phase DNA synthesis techniques, monomers are prepared according to reaction Scheme I or II.

Reaction Scheme I

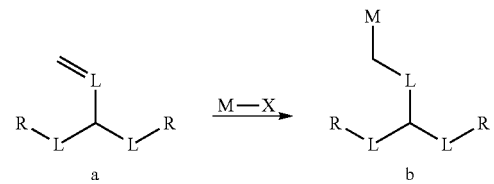

Reaction Scheme I illustrates an exemplary method for preparing an intermediate useful for preparing polymers disclosed herein, where each R is independently a protected alcohol, each L is independently an optional linker, and M is a fluorescent or colored moiety. Referring to Reaction Scheme 1, compounds of structure a are purchased or prepared by methods well-known to those of ordinary skill in the art. Reaction of a with M-X, where X is a halogen such as bromo, under Suzuki coupling conditions known in the art results in compounds of structure b. Compounds of structure b are then converted to phosphoramadites according to methods known in the art.

Reaction Scheme II

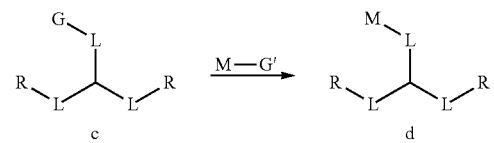

Reaction Scheme II illustrates an alternative method for preparation of monomers useful for preparation of the polymers. Referring to reaction Scheme II, where $R^1$ L and M are as defined above in Reaction Scheme I, a compound of structure c, which can be purchased or prepared by well-known techniques, is reacted with M-G' to yield compounds of structure d. Here, G and G' represent functional groups having complementary reactivity (i.e., functional groups, such as click functional groups, which react to form a covalent bond). G' may be pendant to M or a part of the structural backbone of M. G may be any number of functional groups described herein, such as alkyne, and G' may be azide. In some embodiments, G and G' are alkyne and azide, respectively, amine and activated ester, respectively or amine and isothiocyanate, respectively, and the like. Phosphoramidites of compound d are prepared according to well-known techniques.

The thus prepared phosphoramidites are incorporated into polymer using known DNA synthesis techniques and using phosphoramidites having the desired functionality to result in a polymer having (or can be modified to have) the charged moieties. DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

In certain embodiments, the polymer comprising a peptide backbone. Such peptide-based polymer can be prepared according to established solid-phase peptide methods, and the charged, fluorescent and/or colored moieties are introduced as monomers or after preparation of the backbone. For example, exemplary peptide-based polymers are prepared according to reaction Scheme III below, where PG is a suitable protecting group, X is linkage to a solid support, the shaded circle is a suitable solid support, and M is the fluorescent or colored moiety.

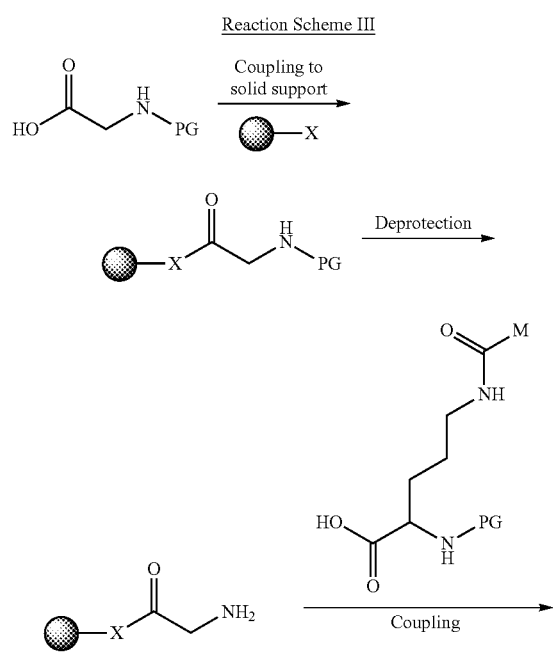

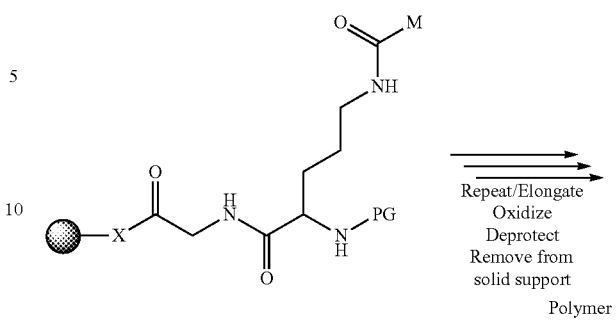

Referring to Reaction Scheme III, small porous beads are initially treated with functional units, which bind to the surface of the porous beads. Peptide chains are built upon the functional units sites and remain covalently bonded to the bead until they are cleaved. When attached, a peptide chain is immobilized on the solid phase and retained during a filtration process, wherein liquid reagents and by-products of the synthesis are washed away.

The general cycle of solid phase synthesis is one of repeated cycles of deprotection-wash-coupling-wash. A free N-terminal amine of a peptide, attached to a solid support, is coupled to an N-protected amino acid group (e.g., with Fmoc or Boc). The newly introduced amino acid unit is deprotected to reveal a new N-terminal amine, which is further reacted with additional amino acids. The process is repeated and the peptide chain is elongated.

When the peptide chain has incorporated all desired amino acid and monomer units, it is cleaved from the bead. Cleaving reagents such as anhydrous hydrogen fluoride or trifluoroacetic acid can be used to cleave peptide chains from beads. The peptide chain is then collected, purified and characterized.

The charged moieties are introduced as amino acid monomers or by modification of the resulting peptide. Alternatively, a peptide is prepared according to the above scheme, and then modified to include M instead of adding M at the monomer level as depicted above.

EXAMPLES

General Methods

Mass spectral analysis is performed on a Waters/Micromass Quattro micro MS/MS system (in MS only mode) using MassLynx 4.1 acquisition software. Mobile phase used for LC/MS is 100 mM 1,1,1,3,3,3-hexafluoro-2-propanol (HFIP), 8.6 mM triethylamine (TEA), pH 8. Phosphoramidites and precursor molecules are also analyzed using a Waters Acquity UHPLC system with a 2.1 mm×50 mm Acquity BEH-C18 column held at 45° C., employing an acetonitrile/water mobile phase gradient. Molecular weights for monomer intermediates are obtained using tropylium cation infusion enhanced ionization on a Waters/Micromass Quattro micro MS/MS system (in MS only mode). Excitation and emission profiles experiments are recorded on a Cary Eclipse spectra photometer.

All reactions are carried out in oven dried glassware under a nitrogen atmosphere unless otherwise stated. Commercially available DNA synthesis reagents are purchased from Glen Research (Sterling, Va.). Anhydrous pyridine, toluene, dichloromethane, diisopropylethyl amine, triethylamine, acetic acid, pyridine, and THF are purchased from Aldrich. All other chemicals are purchase from Aldrich or TCI and are used as is with no additional purification.

Example 1

Synthesis of Polymers Via Solid-Phase DNA Techniques

Polymers are synthesized on an Applied Biosystems 394 DNA/RNA synthesizer on 1 µmol scale and have a 3'-phosphate group or 3'-$S_2$—$(CH_2)_6$—OH group. Synthesis is performed directly on CPG beads or on Polystyrene solid support. The polymers are synthesized in the 3' to 5' direction using standard solid phase DNA methods, and coupling employing standard β-cyanoethyl phosphoramidite chemistry. Phosphoramidite, spacers and linkers are dissolved in acetonitrile to make 0.1 M solutions, and are added in successive order using the following synthesis cycle: 1) removal of the 5'-dimethoxytrityl protecting group with dichloroacetic acid in dichloromethane, 2) coupling of the next phosphoramidite with activator reagent in acetonitrile, 3) oxidation of P(III) to form stable P(v) with iodine/pyridine/water, and 4) capping of any unreacted 5'-hydroxyl groups with acetic anhydride/1-methylimidizole/acetonitrile. The synthesis cycle is repeated until the full length polymer is assembled. At the end of the chain assembly, the monomethoxytrityl (MMT) group or dimethoxytrityl (DMT) group is removed with dichloroacetic acid in dichloromethane.

The compounds are provided on controlled-pore glass (CPG) support at 0.2 umol scale in a labeled Eppendorf tube. 400 µL of 20-30% $NH_4OH$ is added and mixed gently. Open tubes are placed at 55° C. for ~5 minutes or until excess gases had been liberated, and then are closed tightly and incubated for 2 hrs (+/−15 min.). Tubes are removed from the heat block and allowed to reach room temperature, followed by centrifugation at 13,400 RPM for 30 seconds to consolidate the supernatant and solids. Supernatant is carefully removed and placed into a labeled tube, and then 1504, acetonitrile is added to wash the support. After the wash is added to the tubes they are placed into a CentriVap apparatus at 40° C. until dried.

Charged, fluorescent, and/or colored moieties are added as phosphoramidites during the polymerization reaction or by post-polymerization modification (before or after removal from the solid support).

The products are characterized by ESI-MS, UV-absorbance, and fluorescence spectroscopy.

Example 2

Preparation of Polymers Having DNA-Based Backbone

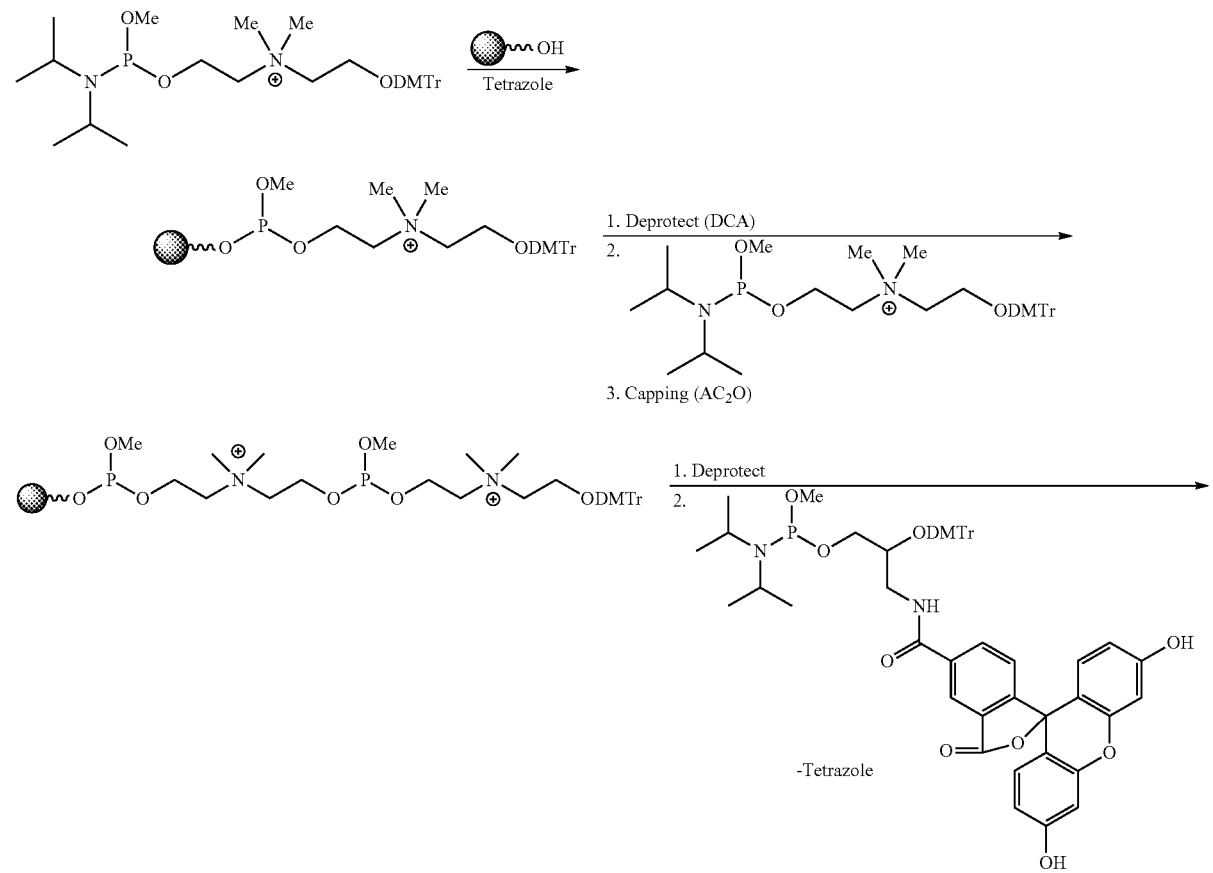

-continued

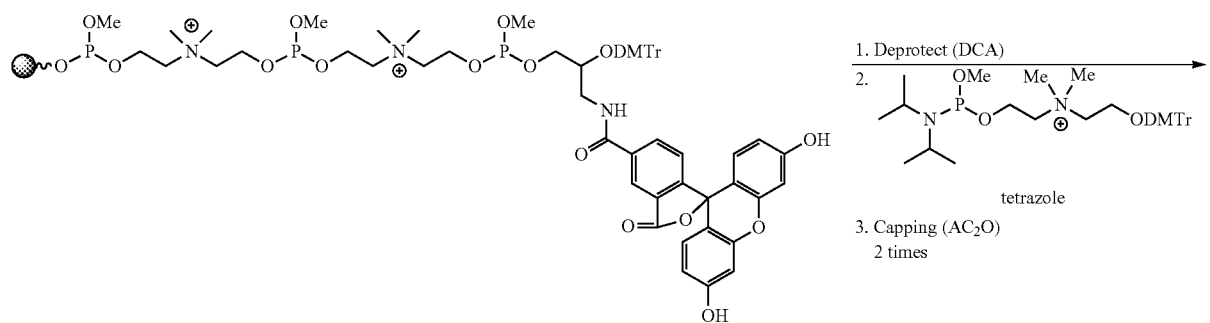

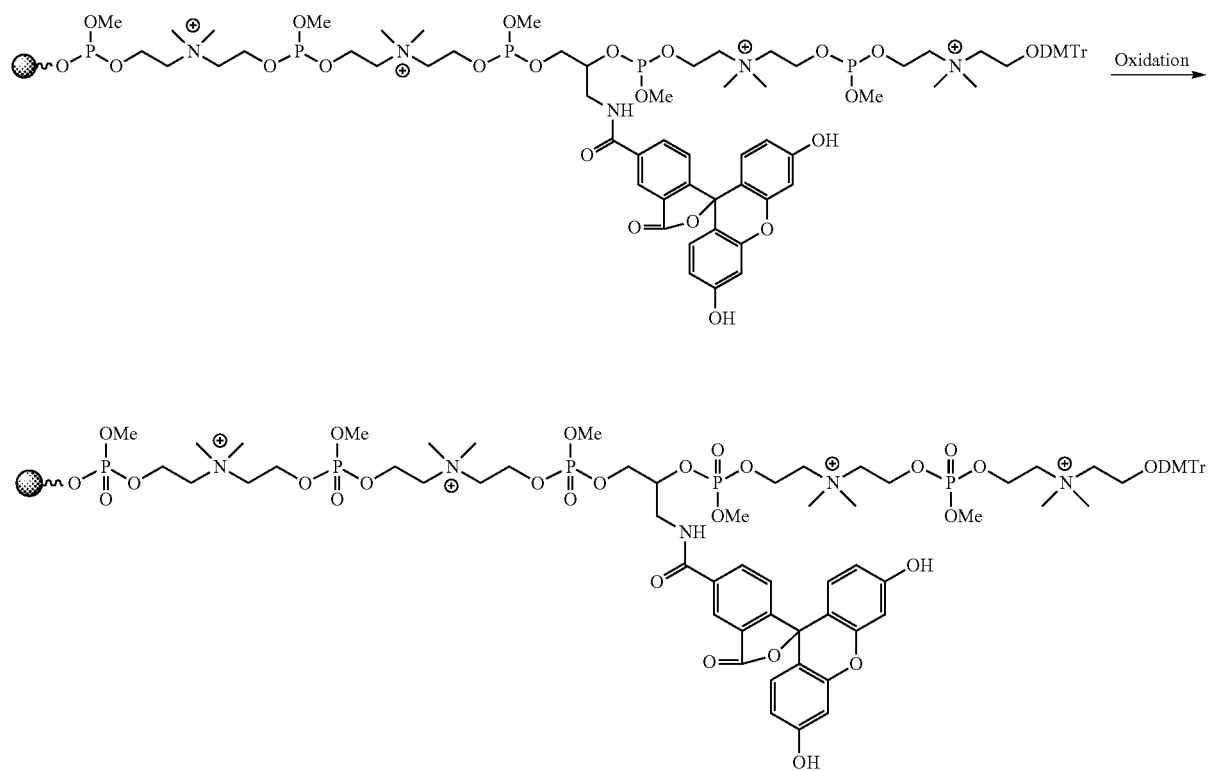

Exemplary polymers comprising positive charge within the backbone are prepared according to the above synthetic scheme. The coupling steps are repeated the desired number of times to produce a polymer of desired length and number of charges and fluorescent and/or colored moieties.

Other polymers with charges within the backbone are prepared as illustrated above, but using the following spermine phosphoramidite (available commercially from Polyplus and/or Glenn Research).

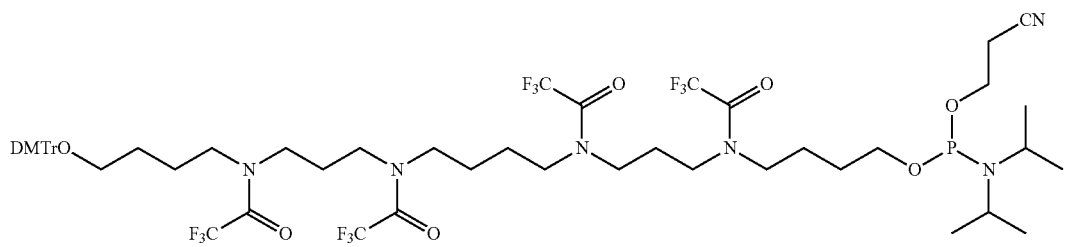

The trifluoroacetyl protecting group in the above phosphoramidite is removed after coupling, and the free amine is protonated or per-alkylated to obtain a positively charged nitrogen group.

Polymers having charges pendant to the polymer backbone are prepare according to analogous procedures, but with one of the following phosphoramidites:

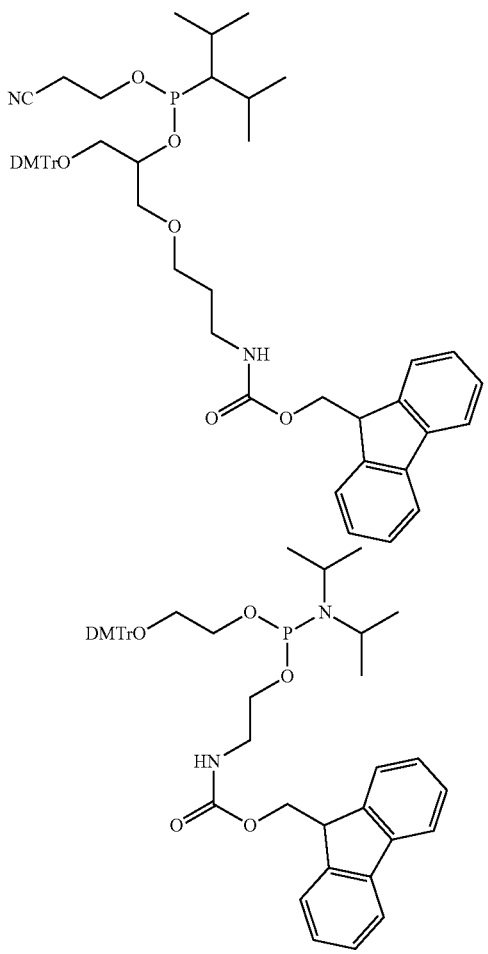

Following incorporation into the polymer, the F-moc protecting group in the above phosphoramidites is removed using standard chemistry. The free amine is then protonated or peralkylated to obtain a pending positive charge.

Example 3

Preparation of Polymers Having a Peptide-Based Backbone

Appropriately protected amino acids having one of the following structures:

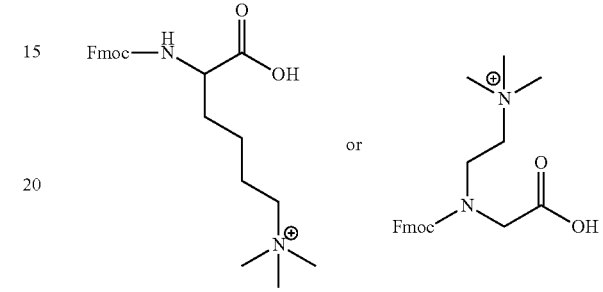

are incorporated into a peptide using solid-phase techniques as known in the art and described herein. The free amine analogue of one or both of the above amino acids is also incorporated into the peptide and the free amine is acylated with an appropriate fluorescent or colored moiety comprising a carboxylic acid. Alternatively, the free amine analogues of one or both of the above amino acids is incorporated into a peptide and some of the free amines are then protonated or peralkylated to include a positive charge and other of the free amines are acylated with an appropriate fluorescent or colored moiety.

To prepare a polymer with a peptide backbone and negatively charged moieties, polyglutamic acid is first prepared. A portion of the free carboxylic acid moieties are then coupled, for example by amide coupling, with an amine-containing fluorescent or colored moiety to prepare the final polymer.

Example 4

Preparation of Polymers by Atom Transfer Radical Polymerization

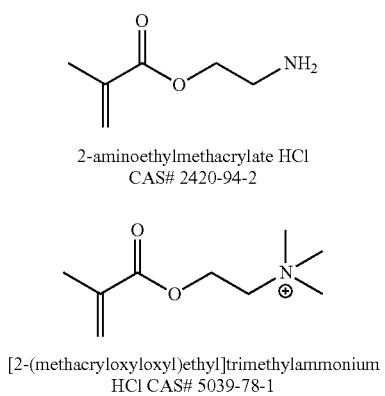

2-aminoethylmethacrylate HCl
CAS# 2420-94-2

[2-(methacryloxyloxyl)ethyl]trimethylammonium
HCl CAS# 5039-78-1

-continued

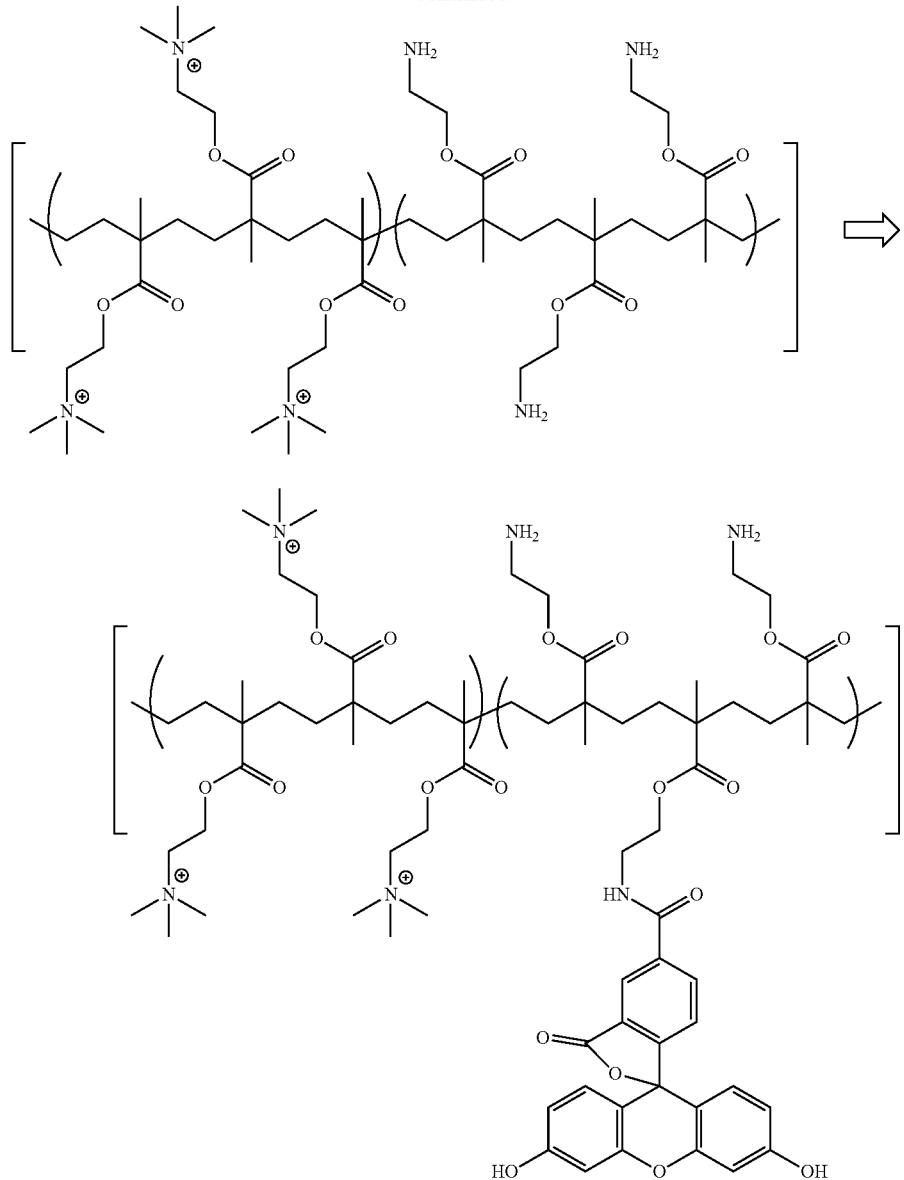

2-aminoethylmethacrylate and 2-(methacryloxy)ethyltrimethylammonium are copolymerized according to the above scheme. One or more of the free amines in the polymerized product is acylated with a fluorescent or colored moiety to produce the desired polymer.

Example 5

Spectral Testing of Compounds

Dried polymers are reconstituted in 150 µL of 0.1M $Na_2CO_3$ buffer to make a ~1 mM stock. The concentrated stock is diluted 50× in 0.1×PBS and analyzed on a NanoDrop UV spectrometer to get an absorbance reading. Absorbance readings are used along with the extinction coefficient (75,000 $M^{-1}$ $cm^{-1}$ for each FAM unit) and Beer's Law to determine an actual concentration of the stock. From the calculated stock concentrations, ~4 mL of a 5 µM solution is made in 0.1M $Na_2CO_3$ (pH 9) and analyzed in a 1×1 cm quartz cuvette on a Cary 60 UV spectrometer, using a spectral range of 300 nm to 700 nm, to gauge overall absorbance relative to the group. From these 5 µM solutions, a second dilution is made at either 50 nM or 25 nM (also in 0.1M $Na_2CO_3$, pH 9) for spectral analysis on a Cary Eclipse Fluorimeter. Excitation is set at 494 nm and emission spectra are collected from 499 to 700 nm.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A polymer comprising:
   i) a backbone;
   ii) two or more positively charged moieties on the backbone; and
   iii) first and second colored or fluorescent moieties on the backbone, wherein the two or more positively charged moieties are in a position on the polymer backbone between the first and second colored or fluorescent moieties, and having the following structure (I):

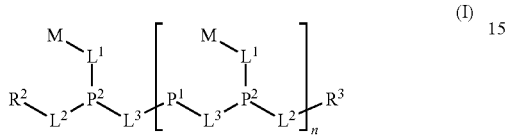

or a stereoisomer, salt or tautomer thereof, wherein:

M is, at each occurrence, independently the fluorescent or colored moiety;

P¹ is, at each occurrence, independently one of the following structures:

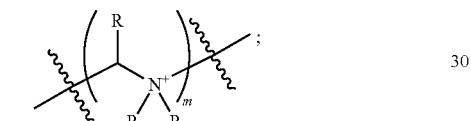

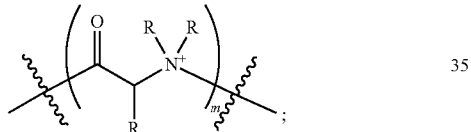

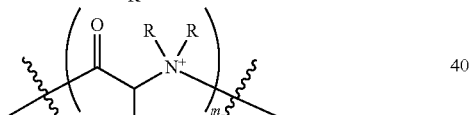

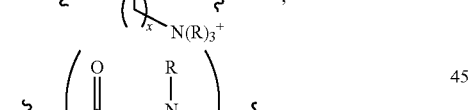

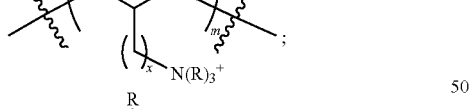

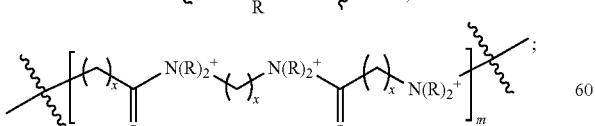

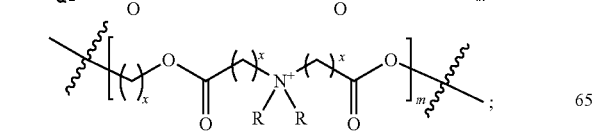

-continued

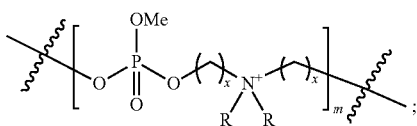

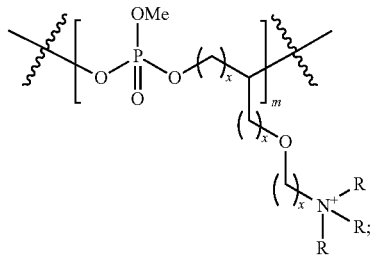

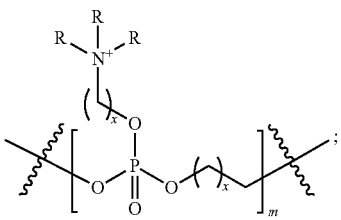

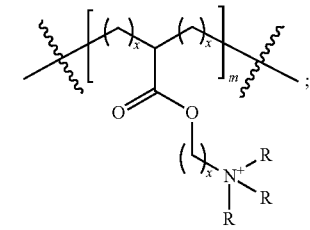

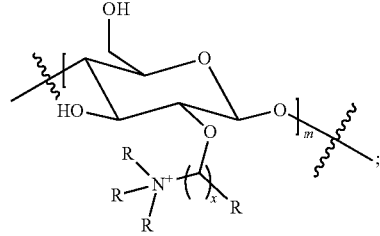

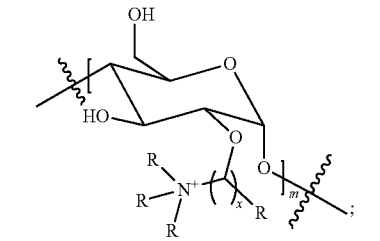

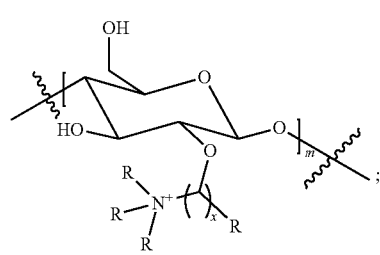

-continued

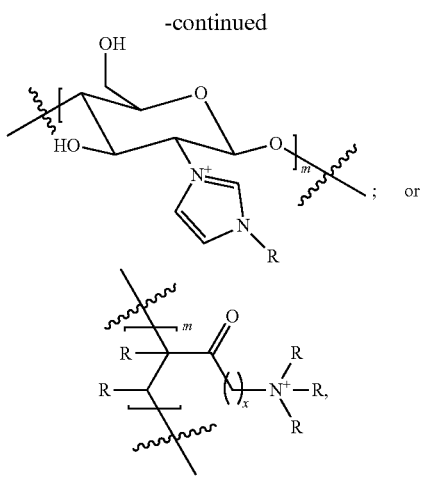

wherein:
R is H or $C_1$-$C_6$ alkyl;
x is an integer from 0 to 6; and
m is an integer of 1 or greater, provided that m is selected such that $P^1$ comprises at least two positively charged moieties;
$P^2$ is, at each occurrence, independently a section of the backbone to which the fluorescent or colored moiety is attached;
$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups, wherein for at least one occurrence of $L^1$, $L^1$-M has one of the following structures:

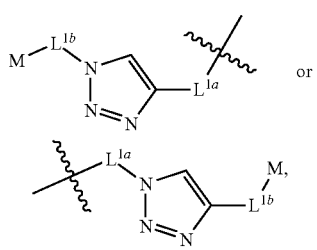

wherein $L^{1a}$ and $L^{1b}$ are each independently optional linkers;
$L^2$ is at each occurrence, independently absent, a section of the backbone or a linker linking $P^2$ to $R^2$ or $P^2$ to $R^3$;
$L^3$ is, at each occurrence, independently an optional linker linking $P^1$ to $P^2$;
$R^2$ and $R^3$ are each independently H, OH, SH, alkyl, alkoxy, alkylether, heteroalkyl, —OP(=$R_a$)($R_b$)$R_c$, Q or L';
$R_a$ is O or S;
$R_b$ is OH, SH, O⁻, S⁻, $OR_d$ or $SR_d$;
$R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;
$R_d$ is a counter ion;
Q is, at each occurrence, independently a moiety comprising a sulfhydryl, disulfide, N-succinimide ester, imidoester, polyflourophenyl ester, isothiocyanate, alkyl azide, an acyl azide, alkyne, alkene, diene, dienophile, acid halide, sulfonyl halide, phosphine, α-haloamide, biotin, amino, maleimide functional group, or a moiety selected from one of the following structures:

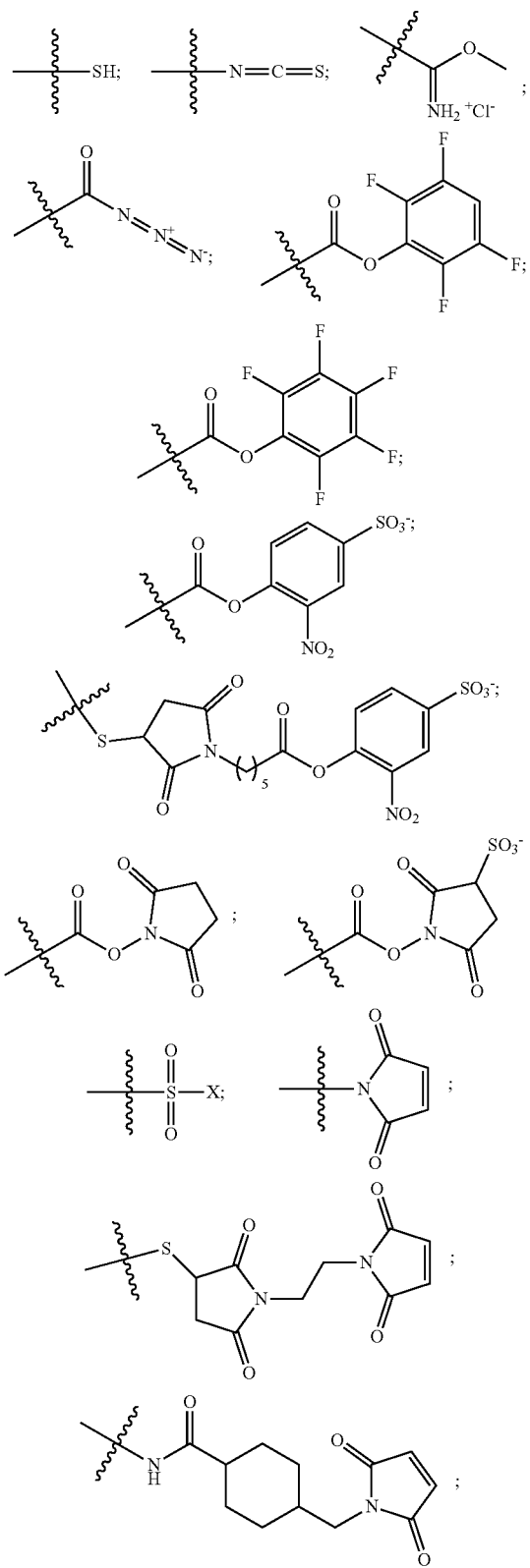

-continued

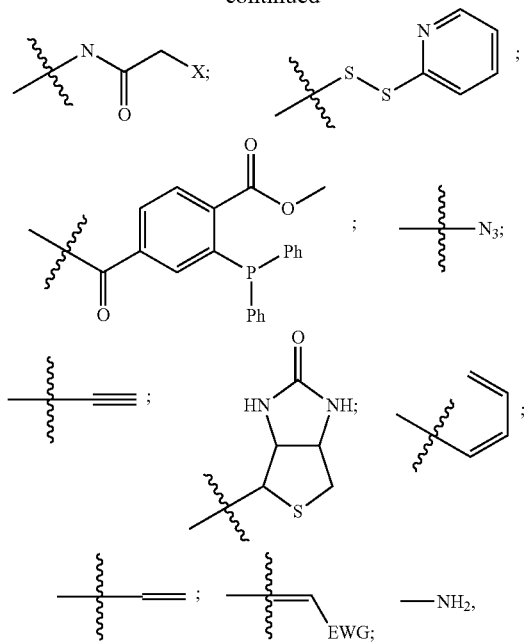

wherein:
X is halo; and
EWG is an electron withdrawing group;
L¹ is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I); and
n is an integer of one or greater.

2. The polymer of claim 1, wherein $L^2$ and $L^3$ are, at each occurrence, independently $C_1$-$C_6$ alkylene, $C_2$-$C_6$ alkenylene or $C_2$-$C_6$ alkynylene.

3. The polymer of claim 1, wherein $R^2$ and $R^3$ are each independently OH or —OP($=R_a$)($R_b$)$R_c$.

4. The polymer of claim 1, wherein one of $R^2$ and $R^3$ is OH or —OP($=R_a$)($R_b$)$R_c$, and the other of $R^2$ and $R^3$ is Q or a linker comprising a covalent bond to Q.

5. The polymer of claim 1, wherein one of $R^2$ and $R^3$ is OH or —OP($=R_a$)($R_b$)$R_c$, and the other of $R^2$ and $R^3$ is a linker comprising a covalent bond to a nucleic acid or polymer thereof, an amino acid or polymer thereof, an enzyme, receptor, receptor ligand, antibody, glycoprotein, aptamer or prion or a linker comprising a covalent bond to a polymeric bead or non-polymeric bead.

6. The polymer of claim 1, wherein the fluorescent or colored moiety of M is, at each occurrence, independently a dimethylaminostilbene, quinacridone, fluorophenyl-dimethyl-BODIPY, bis-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety.

7. The polymer of claim 1, wherein the fluorescent or colored moiety of M is, at each occurrence, independently p-terphenyl, perylene, azobenzene, phenazine, phenanthroline, acridine, thioxanthrene, chrysene, rubrene, coronene, cyanine, perylene imide, or perylene amide or a derivative of perylene, acridine, cyanine, perylene imide, or perylene amide.

8. The polymer of claim 1, wherein the fluorescent or colored moiety of M is, at each occurrence, independently a coumarin dye, resorufin dye, dipyrromethene boron difluoride dye, ruthenium bipyridyl dye, energy transfer dye, thiazole orange dye, polymethine or N-aryl-1,8-naphthalimide dye.

9. The polymer of claim 1, wherein the fluorescent or colored moiety of M is, at each occurrence, independently pyrene, perylene, perylene monoimide or 6-FAM or a derivative of pyrene, perylene, or perylene monoimide.

10. The polymer of claim 1, wherein the fluorescent or colored moiety of M is, at each occurrence, independently has one of the following structures:

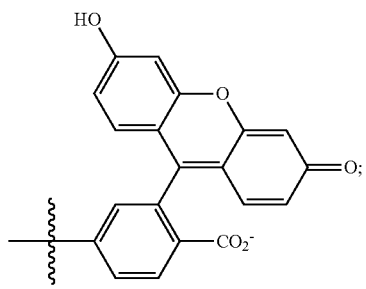

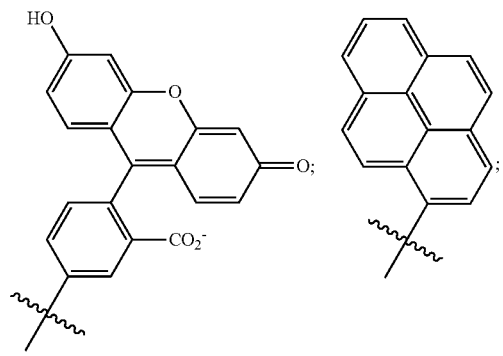

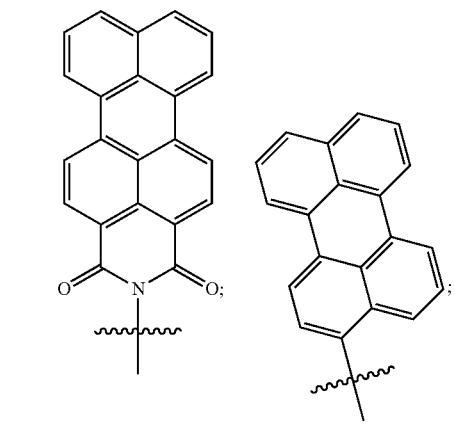

-continued
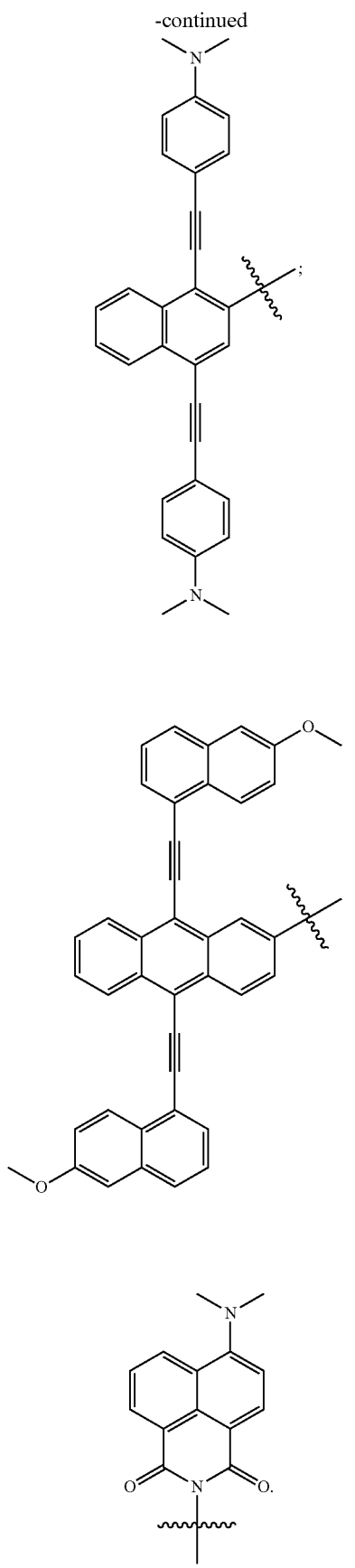
11. A polymer having one of the following structures:
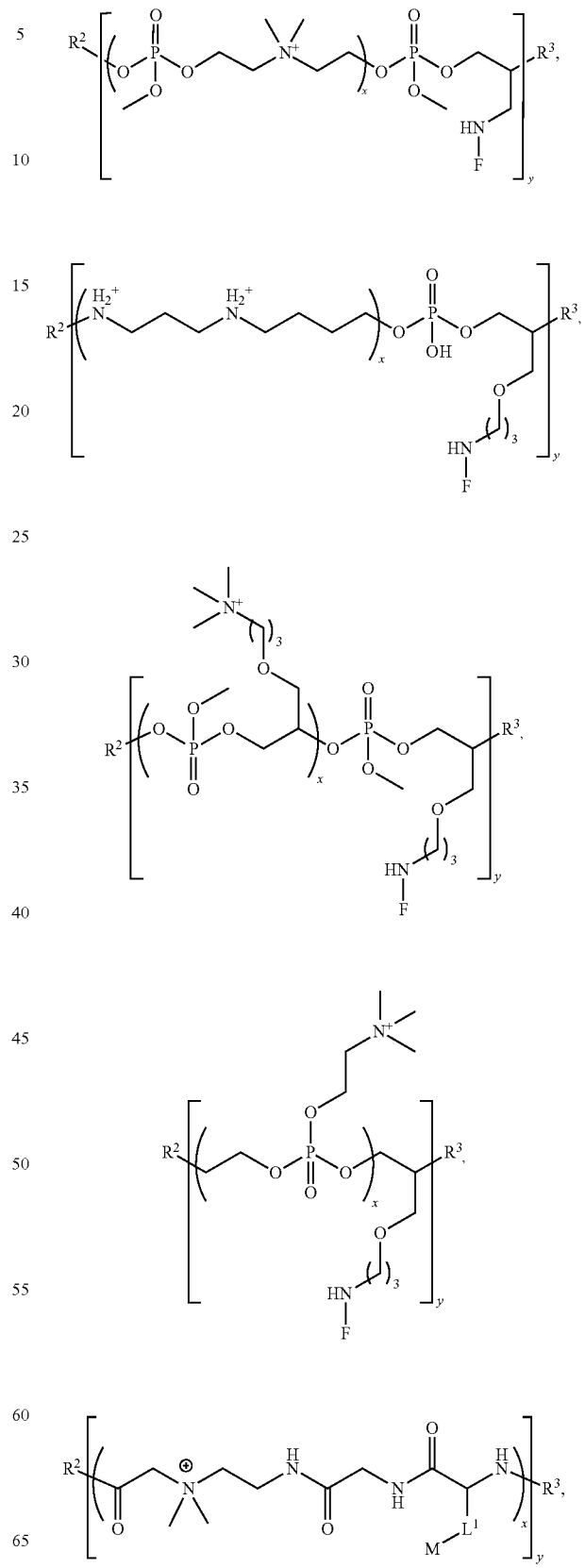

-continued

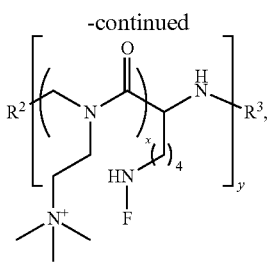

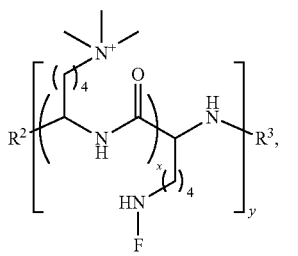

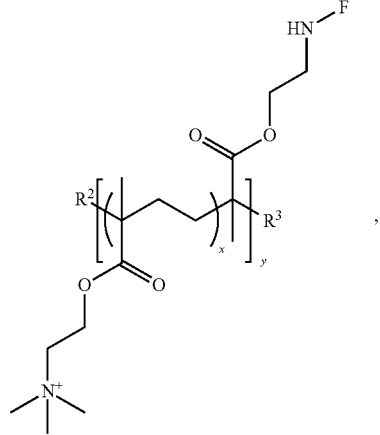

wherein:
x is, at each occurrence, independently an integer of 1 or greater, provided that x is selected such that the compound includes at least two positively charged moieties for at least one integral value of y;
y is an integer of 2 or greater;
$R^2$, $R^3$ and $L^1$ are defined according to claim 1; and
F is a fluorescein moiety having the following structure:

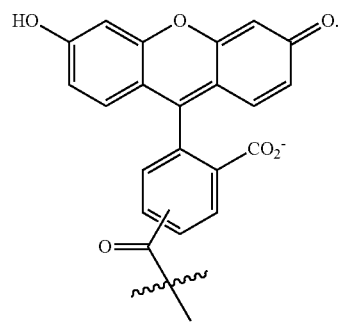

12. A method of staining a sample, comprising adding to said sample the polymer of claim 1 in an amount sufficient to produce an optical response when said sample is illuminated at an appropriate wavelength.

13. The method of claim 12, wherein said optical response is a fluorescent response, the sample comprises cells, and the method further comprises observing the cells by flow cytometry.

14. A method for visually detecting an analyte molecule, the method comprising:
(a) providing the polymer of claim 1, wherein the polymer comprises a covalent bond to the analyte molecule; and
(b) detecting the polymer by its visible properties.

* * * * *

UNITED STATES PATENT AND TRADEMARK OFFICE
CERTIFICATE OF CORRECTION

PATENT NO. : 11,377,563 B2
APPLICATION NO. : 16/307876
DATED : July 5, 2022
INVENTOR(S) : Tracy Matray et al.

Page 1 of 1

It is certified that error appears in the above-identified patent and that said Letters Patent is hereby corrected as shown below:

In the Claims

<u>Column 54, Claim 10, Line 19:</u>
"colored moiety of M is, at each occurrence, independently"
Should read:
--colored moiety of M, at each occurrence, independently--.

Signed and Sealed this
Fourteenth Day of January, 2025

Derrick Brent
*Acting Director of the United States Patent and Trademark Office*